(12) United States Patent
Scianamblo

(10) Patent No.: US 10,595,961 B2
(45) Date of Patent: Mar. 24, 2020

(54) ENDODONTIC INSTRUMENTS DISPLAYING COMPRESSIBILITY

(71) Applicant: Michael J. Scianamblo, Tiburon, CA (US)

(72) Inventor: Michael J. Scianamblo, Tiburon, CA (US)

(*) Notice: Subject to any disclaimer, the term of this patent is extended or adjusted under 35 U.S.C. 154(b) by 0 days.

(21) Appl. No.: 15/470,211

(22) Filed: Mar. 27, 2017

(65) Prior Publication Data

US 2017/0209236 A1  Jul. 27, 2017

(51) Int. Cl.
| | |
|---|---|
| A61C 5/40 | (2017.01) |
| A61C 3/02 | (2006.01) |
| A61C 5/42 | (2017.01) |
| A61C 5/00 | (2017.01) |

(52) U.S. Cl.
CPC ............... *A61C 5/40* (2017.02); *A61C 3/02* (2013.01); *A61C 5/42* (2017.02); *A61C 5/00* (2013.01)

(58) Field of Classification Search
CPC .............. A61C 5/40; A61C 5/00; A61C 3/02
USPC ........................................................ 433/224
See application file for complete search history.

(56) References Cited

U.S. PATENT DOCUMENTS

| | | | |
|---|---|---|---|
| 4,044,468 A | 8/1977 | Kahn | |
| 4,260,379 A | 4/1981 | Graves | |
| 4,332,561 A | 6/1982 | McSpadden | |
| 4,353,698 A | 10/1982 | McSpadden | |
| 4,457,710 A | 7/1984 | McSpadden | |
| 4,536,159 A | 8/1985 | Roane | |
| 4,538,989 A | 9/1985 | Apairo, Jr. et al. | |
| 4,889,487 A | 12/1989 | Lovaas | |
| 4,934,934 A | 6/1990 | Arpaio, Jr. et al. | |
| 4,992,048 A | 2/1991 | Goof | |
| 5,106,298 A | 4/1992 | Heath et al. | |
| 5,464,362 A | 11/1995 | Heath et al. | |
| 5,498,158 A | 3/1996 | Wong | |
| 5,503,554 A | 4/1996 | Schoeffel | |
| 5,605,460 A | 2/1997 | Heath et al. | |
| 5,653,590 A | 8/1997 | Heath et al. | |

(Continued)

FOREIGN PATENT DOCUMENTS

| | | |
|---|---|---|
| EP | 0 120 542 | 10/1984 |
| EP | 1 184 004 | 3/2002 |

(Continued)

OTHER PUBLICATIONS

International Search Report and Written Opinion in Application No. PCT/US18/23758, dated Jun. 15, 2018, 12 pages.

(Continued)

*Primary Examiner* — Sean M Michalski
*Assistant Examiner* — Mirayda A Aponte
(74) *Attorney, Agent, or Firm* — Fish & Richardson P.C.

(57) ABSTRACT

Endodontic instruments are used to clean and enlarge the endodontic cavity space (ECS), also known as the root canal system, of a human tooth. This document describes novel endodontic instruments that are radially compressible, and methods for their use. Some embodiments include a shank and a body with a working surface. At least a portion of the working surface may define a center of mass path that spirals. The center of mass of a transverse cross-section of the working surface at the shank end can be offset from the axis of rotation of the instrument.

15 Claims, 26 Drawing Sheets

(56) References Cited

U.S. PATENT DOCUMENTS

| | | |
|---|---|---|
| 5,658,145 A | 8/1997 | Maillefer et al. |
| 5,676,541 A | 10/1997 | Maillefer et al. |
| 5,752,825 A | 5/1998 | Buchanan |
| 5,775,904 A | 7/1998 | Riitano |
| 5,836,764 A | 11/1998 | Buchanan |
| 5,842,862 A | 12/1998 | Nissan |
| 5,882,198 A | 3/1999 | Taylor et al. |
| 5,897,316 A | 4/1999 | Buchanan |
| 5,902,106 A | 5/1999 | McSpadden |
| 5,921,775 A | 7/1999 | Buchanan |
| 5,938,440 A | 8/1999 | McSpadden |
| 5,984,679 A | 11/1999 | Farzin-Nia et al. |
| 6,074,209 A | 6/2000 | Johnson |
| 6,106,296 A | 8/2000 | Johnson |
| 6,293,794 B1 | 9/2001 | McSpadden |
| 6,299,445 B1 | 10/2001 | Garman |
| 6,315,558 B1 | 11/2001 | Farzin-Nia et al. |
| 6,409,506 B1 | 6/2002 | Graybill |
| 6,419,488 B1 | 7/2002 | McSpadden et al. |
| 6,575,748 B1 | 6/2003 | Filhol |
| 6,702,579 B1 | 3/2004 | Hoppe et al. |
| 6,712,611 B2 | 3/2004 | Garman |
| 6,890,134 B1 | 5/2005 | Wagner et al. |
| 6,929,078 B1 | 8/2005 | Randall |
| 6,942,484 B2 | 9/2005 | Scianamblo |
| 7,094,056 B2 | 8/2006 | Scianamblo |
| 7,125,252 B2 | 10/2006 | Rouiller et al. |
| 7,232,311 B1 | 6/2007 | Greggs |
| 7,955,078 B2 | 6/2011 | Scianamblo |
| 8,454,361 B2 | 6/2013 | Scianamblo |
| 8,496,476 B2 | 7/2013 | Scianamblo |
| D710,009 S | 7/2014 | Maupin |
| 8,882,504 B2 | 11/2014 | Scianamblo |
| 8,916,009 B2 | 12/2014 | Ammon et al. |
| 8,932,056 B2 | 1/2015 | Scianamblo |
| 9,078,722 B2 | 7/2015 | Johnson |
| D750,246 S | 2/2016 | Scianamblo |
| 9,351,803 B2 | 5/2016 | Scianamblo |
| 9,801,696 B2 | 10/2017 | Rota et al. |
| 2003/0068597 A1 | 4/2003 | Garman |
| 2004/0023186 A1 | 2/2004 | McSpadden |
| 2004/0131993 A1 | 7/2004 | Rouiller et al. |
| 2004/0185414 A1 | 9/2004 | Badoz |
| 2004/0191723 A1 | 9/2004 | Shearer |
| 2004/0265775 A1 | 12/2004 | Maillefer et al. |
| 2005/0026109 A1 | 2/2005 | Buchanan |
| 2005/0266375 A1 | 12/2005 | Brock et al. |
| 2006/0228668 A1 | 10/2006 | McSpadden |
| 2006/0228669 A1* | 10/2006 | Scianamblo ............ A61C 5/023 433/102 |
| 2007/0059663 A1 | 3/2007 | Scianamblo |
| 2007/0184406 A1 | 8/2007 | Mason |
| 2012/0219927 A1 | 8/2012 | Maxwell et al. |
| 2013/0189644 A1* | 7/2013 | Johnson ................. A61C 5/42 433/102 |
| 2013/0302749 A1 | 11/2013 | Scianamblo |
| 2015/0057664 A1* | 2/2015 | Scianamblo ........ B23B 51/0081 606/80 |
| 2015/0072307 A1 | 3/2015 | Scianamblo |
| 2015/0230902 A1 | 8/2015 | Andreou |
| 2015/0320517 A1* | 11/2015 | Rota ........................ A61C 5/42 433/102 |

FOREIGN PATENT DOCUMENTS

| | | |
|---|---|---|
| FR | 2 798 277 | 3/2001 |
| WO | WO 02/065938 | 8/2002 |
| WO | WO 04/098438 | 11/2004 |

OTHER PUBLICATIONS

Partial European Search Report, European Application Serial No. EP 06 00 7527, dated Jun. 26, 2006, 6 pages.

EP 04 75 1290 Supplementary European Search Report, dated Jun. 5, 2007, 5 pages.

EP 04 75 0878 Supplementary European Search Report, dated Jun. 5, 2007, 3 pages.

Communication pursuant to Article 94(3) EPC for Application No. EP 06 00 7527.2-1265, dated Jun. 17, 2009, 5 pages.

Linear definition from Merriam-Webster on-line. Retrieved Feb. 20, 2009, from http://www.merriam-webster.com/dictionary/linear, 3 pages.

Revolve. (n.d.). Dictionary.com Unabridged. Retrieved Sep. 23, 2015, from Dictionary.com website: http://dictionary.reference.com/browse/revolve.

Straight. (n.d.). Dictionary.com Unabridged. Retrieved Feb. 11, 2010, from Dictionary.com website: http://dictionary.reference.com/browse/straight, 12 pages.

USPTO Non-Final Office Action in U.S. Appl. No. 11/402,207, dated Feb. 26, 2009, 16 pages.

USPTO Final Office Action in U.S. Appl. No. 11/402,207, dated Oct. 6, 2009, 9 pages.

USPTO Non-Final Office Action in U.S. Appl. No. 11/402,207, dated Feb. 19, 2010, 10 pages.

USPTO Non-Final Office Action in U.S. Appl. No. 11/226,059, dated Mar. 31, 2008, 5 pages.

USPTO Final Office Action in U.S. Appl. No. 11/226,059, dated May 13, 2009, 8 pages.

USPTO Non-Final Office Action in U.S. Appl. No. 11/226,059, dated Oct. 21, 2009, 9 pages.

USPTO Final Office Action in U.S. Appl. No. 11/226,059, dated May 17, 2010, 9 pages.

Office Action in U.S. Appl. No. 11/402,207, dated Aug. 25, 2010, 13 pages.

USPTO Non-Final Office Action in U.S. Appl. No. 11/402,207, dated Aug. 28, 2012, 7 pages.

* cited by examiner

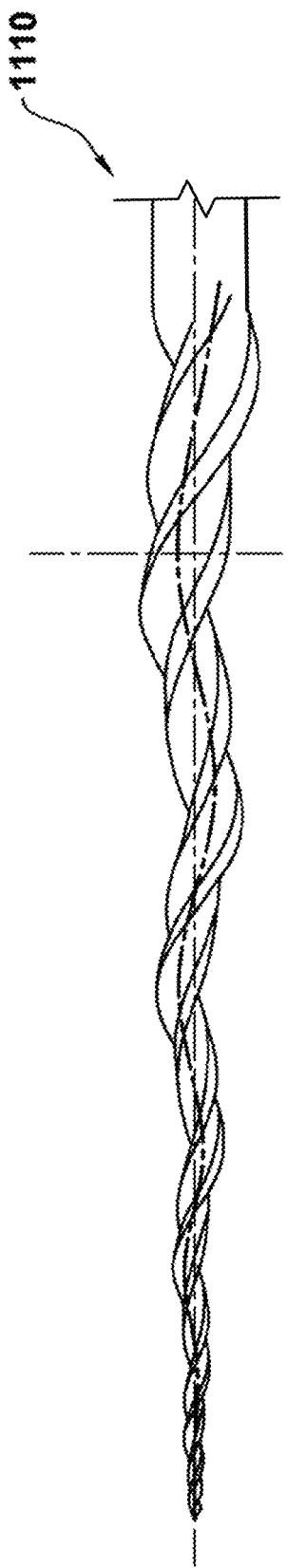
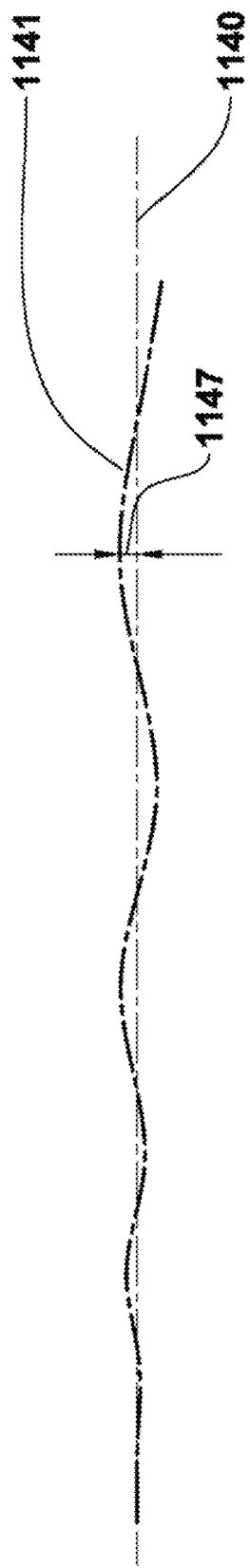
FIG. 11A
FIG. 11B

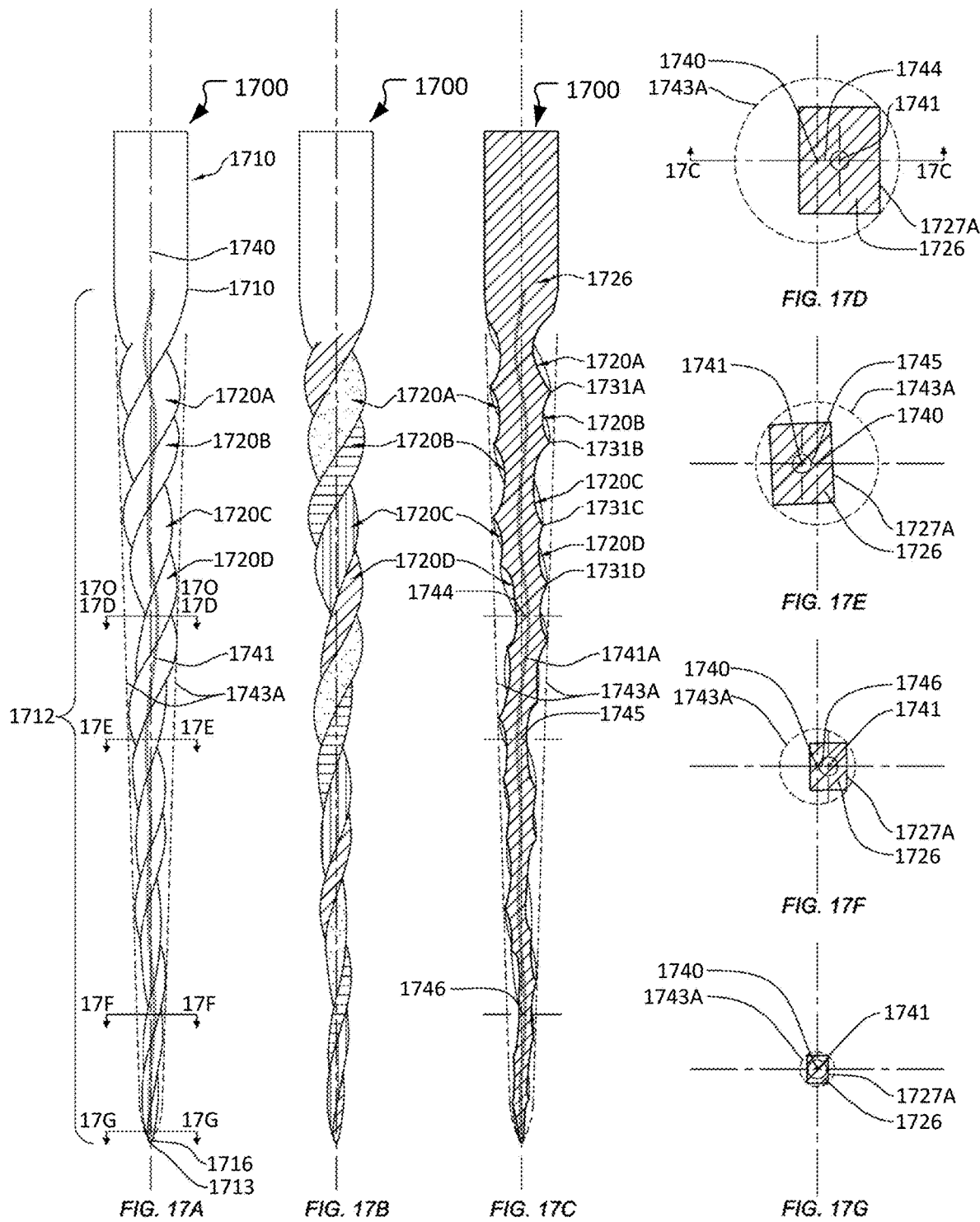

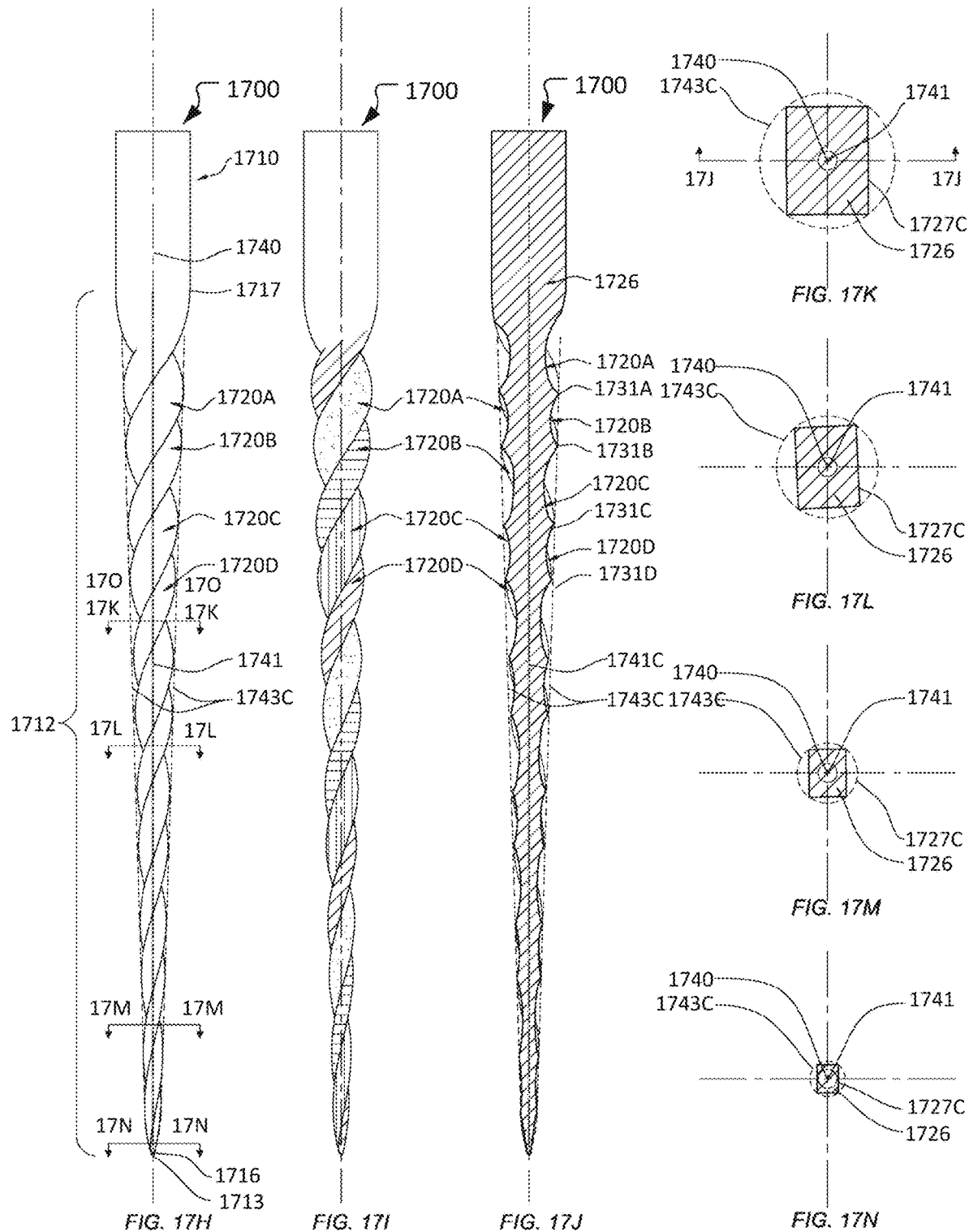

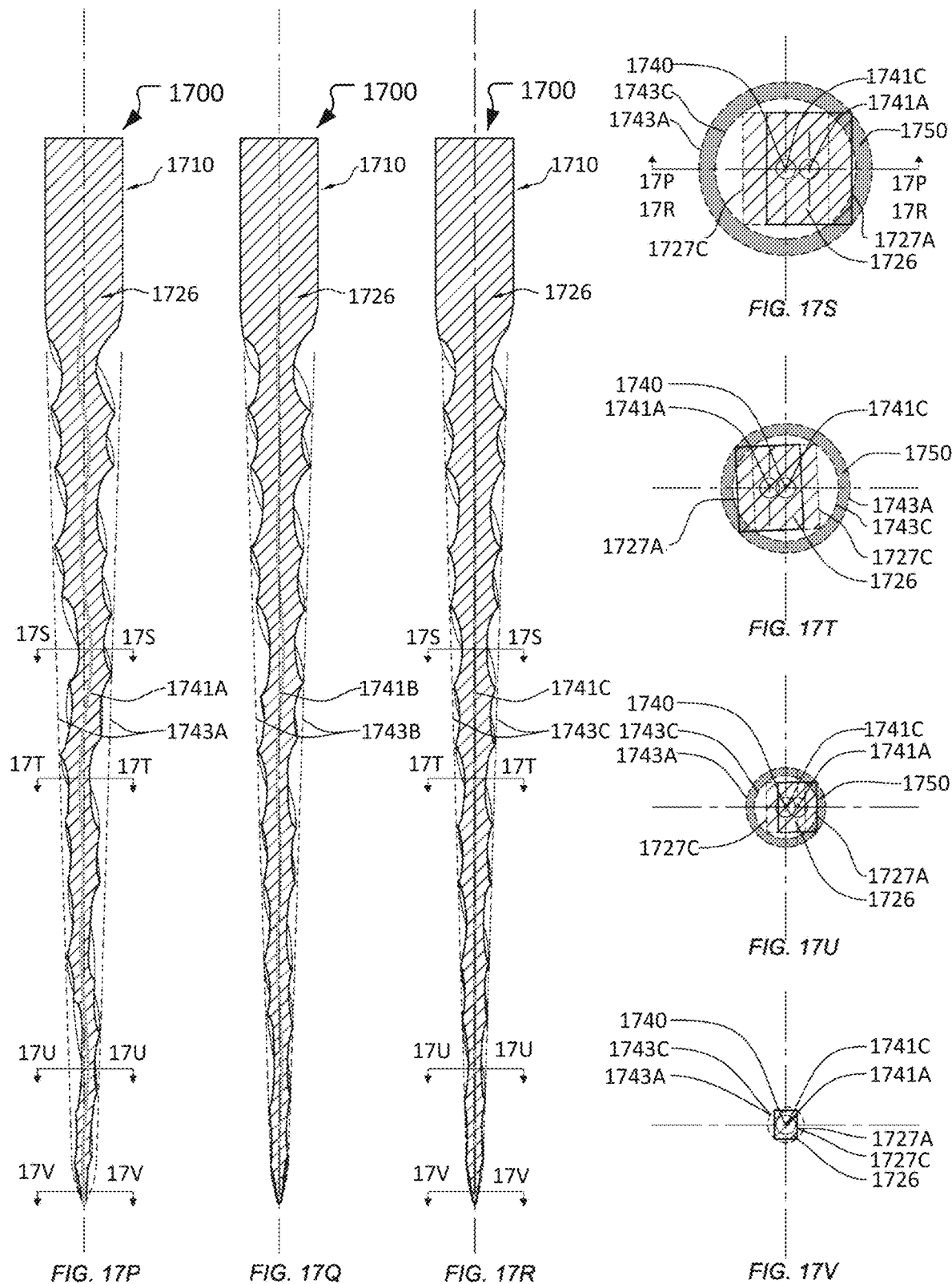

ENDODONTIC INSTRUMENTS DISPLAYING COMPRESSIBILITY

BACKGROUND

1. Technical Field

This document relates to endodontic instruments and methods for their use. For example, this document relates to novel endodontic instruments that are radially compressible and methods for their use.

2. Background Information

Endodontic instruments can be used for cleaning and enlarging the endodontic cavity space (ECS), also known as the root canal system of a human tooth. Much of the background of endodontic instrument design and development, including numerous improvements in design and functionality, has been described by the Applicant in detail in previous patent applications and grants, such as: U.S. Pat. No. 9,351,803 (titled "Endodontic Instruments with Offset Centers of Mass), U.S. Pat. No. D750,246 (titled "Endodontic Device"), U.S. Pat. No. 8,932,056 (titled "Swaggering Endodontic Instruments"), U.S. Pat. No. 8,882,504 (titled "Swaggering Endodontic Instruments"), U.S. Pat. No. 8,496,476 (titled "Endodontic Instruments for Preparing Endodontic Cavity Spaces"), U.S. Pat. No. 8,454,361 (titled "Swaggering Endodontic Instruments"), U.S. Pat. No. 7,955,078 (titled "Endodontic Instruments for Preparing Endodontic Cavity Spaces"), U.S. Pat. No. 7,094,056 (titled "Endodontic Instrument having Reversed Helix"), and U.S. Pat. No. 6,942,484 (titled "Critical Path Endodontic Instruments for Preparing Endodontic Cavity Spaces").

SUMMARY

This document describes endodontic instruments and methods for their use. For example, this document describes novel endodontic instruments that are radially compressible, and methods for their use.

In one aspect, this document is directed to an endodontic instrument that includes a shank configured for attachment to a motor to drive the endodontic instrument about a first axis; and a body extending from the shank by a length. The body is solid and has a working surface between: (i) a shank end where the working surface and the shank meet and (ii) a tip end. The working surface includes multiple edges. At least a portion of the working surface is tapered such that the tip end has a diameter that is less than a diameter of the shank end. The working surface comprises a plurality of transverse cross-sections. Each transverse cross-section has a center of mass and multiple sides. The working surface has a center of mass path defined by the centers of mass of the plurality of transverse cross-sections of the body. At least a portion of the center of mass path between the tip end and the shank end spirals around the first axis along a length of the first axis. A center of mass of a transverse cross-section of the working surface at the shank end is offset from the first axis.

Such an endodontic instrument may optionally include one or more of the following features. The body may be configured such that when the endodontic instrument is driven within the endodontic cavity space about the first axis, at each transverse section of at least a portion of the length of the body, one or more edges of the multiple edges are out of contact with a wall of the endodontic cavity space. The working surface may include a reversed helix. The portion of the center of mass path that spirals around the first axis may extend from the tip end to the shank end. The plurality of transverse cross-sections may include a transverse cross-section that is quadrilateral. Each of the plurality of transverse cross-sections may be quadrilateral. A ratio of lengths of sides of the quadrilateral may remain constant along the length of the body. The plurality of transverse cross-sections may include a transverse cross-section at the tip end that has a center of mass that coincides with the first axis. The plurality of transverse cross-sections may include a transverse cross-section that is triangular. The plurality of transverse cross-sections may include a transverse cross-section that is asymmetrical. The plurality of transverse cross-sections may include a first transverse cross-section and a second transverse cross-section. The first transverse cross-section may have a first geometry, and the second transverse cross-section may have a second geometry different from the first geometry. Each transverse cross-section between the first transverse cross-section and the second transverse cross-section may have a gradually changing geometry with respect to each other. The body may comprise nickel-titanium. The plurality of transverse cross-sections may include a first transverse cross-section and a second transverse cross-section. A center of mass of the first transverse cross-section may be spaced apart from the first axis by a first distance, a center of mass of the second transverse cross-section may be spaced apart from the first axis by a second distance, and the first distance may be greater than the second distance. Each transverse cross-section of the body may be define by a polygonal shape. A ratio of lengths of sides of the polygonal shape may vary along the length of the body. The plurality of transverse cross-sections may include a transverse cross-section at the tip end that has a center of mass that coincides with the first axis.

In another aspect, this disclosure is directed to a method of preparing an endodontic cavity space. The method includes inserting an instrument into the endodontic cavity space; and rotating the instrument about its axis of rotation while the instrument is in the endodontic cavity space. During the rotating the instrument is radially compressed by a wall of the endodontic cavity space.

Such a method may optionally include one or more of the following features. The instrument may include a shank configured for attachment to a motor to drive the endodontic instrument about a first axis; and a body extending from the shank by a length. The body may be solid and has a working surface between: (i) a shank end where the working surface and the shank meet and (ii) a tip end. The working surface may include multiple edges. At least a portion of the working surface may be tapered such that the tip end has a diameter that is less than a diameter of the shank end. The working surface comprises a plurality of transverse cross-sections. Each transverse cross-section may have a center of mass and multiple sides. The working surface may have a center of mass path defined by the centers of mass of the plurality of transverse cross-sections of the body. At least a portion of the center of mass path between the tip end and the shank end may spiral around the first axis along a length of the first axis. A center of mass of a transverse cross-section of the working surface at the shank end may be offset from the first axis. During the rotating the instrument may be radially compressed by the wall of the endodontic cavity space such that the center of mass path is nearer to the axis of rotation than prior to the inserting. During the rotating, one or more edges of the multiple edges may be out of contact with the wall of the endodontic cavity space.

Particular embodiments of the subject matter described in this document can be implemented to realize one or more of the following advantages. In some embodiments, the endodontic instruments described herein can provide more efficient endodontic procedures, and endodontic procedures which are safer for a patient. In some cases, the endodontic instruments described herein are radially compressible, and therefore the efficiency of a procedure can be increased using a single instrument that can advantageously be used in place of a series of multiple instruments of increasing sizes. In some embodiments, the instruments described herein can be made to have a smaller diameter than the space that requires cleaning, thereby allowing for difficult to access areas to be accessed. An instrument that is both flexible and strong resists breaking and injuring the patient. In some embodiments, the instruments are flexible and have a center of mass offset from an axis of rotation that may advantageously swing out from the axis of rotation as the instrument is rotated at high speeds, such as when the instrument is used with a motorized actuator tool.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 11A depicts another example endodontic instrument.
FIG. 11B illustrates the axis of rotation and the center of mass path of the endodontic instrument of FIG. 11A.
FIG. 17A depicts another example endodontic instrument.
FIG. 17B depicts the instrument of FIG. 17A with cross-hatching added to identify the flutes of the instrument.
FIG. 17C is a longitudinal cross-sectional view of the endodontic instrument of FIGS. 17A and 17B.
FIGS. 17D-17G depict cross-sectional views of the endodontic instrument of FIGS. 17A and 17B at cutting-plane lines 17D-17D, 17E-17E, 17F-17F, and 17G-17G respectively.
FIG. 17H corresponds to FIG. 17A while the endodontic instrument is fully radially constrained.
FIG. 17I corresponds to FIG. 17B while the endodontic instrument is fully radially constrained.
FIG. 17J corresponds to FIG. 17C while the endodontic instrument is fully radially constrained.
FIGS. 17K-17N depict cross-sectional views of the endodontic instrument of FIGS. 17H and 17B at cutting-plane lines 17K-17K, 17L-17L, 17M-17M, and 17N-17N respectively.
FIG. 17O-1 depicts the cross-section of FIG. 17O in a fully radially constrained condition.
FIGS. 17P-17R depict another example endodontic instrument longitudinal cross-sectional and at varying conditions of diametrical constraint.
FIGS. 17S-17V depict cross-sectional views of the endodontic instrument of FIGS. 17P and 17Q at cutting-plane lines 17S-17S, 17T-17T, 17U-17U, and 17V-17V respectively.

Like reference numbers represent corresponding parts throughout.

DETAILED DESCRIPTION

Figure 1:
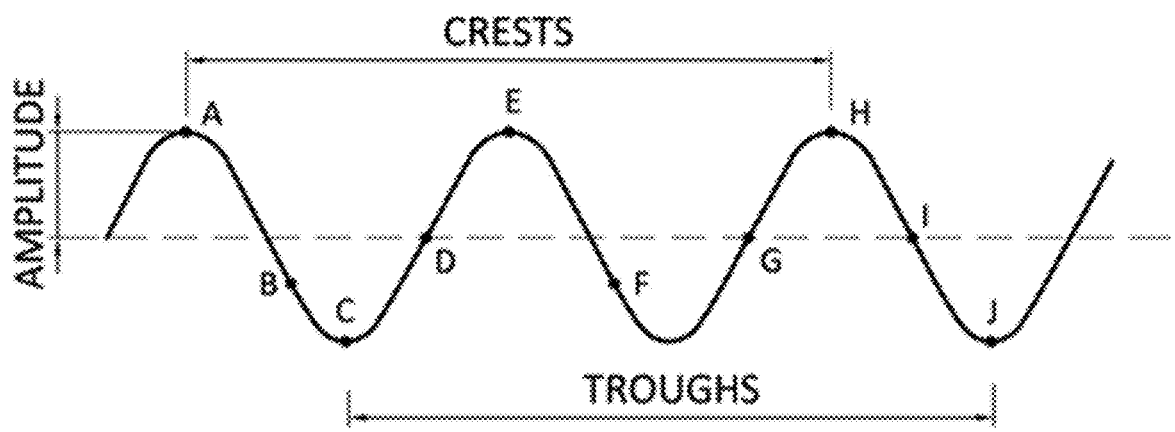
FIG. 1 depicts an example transverse wave pattern.

This document describes endodontic instruments and methods for their use. For example, this document describes novel endodontic instruments that are radially compressible, and methods for their use.

Traditional endodontic instrument designs have a center of rotation and a center of mass that are essentially identical, dictating a linear trajectory or path of motion. These designs facilitate elastic memory and the restoration of the original endodontic instrument shape.

The recent use of nickel-titanium in the manufacture of endodontic instruments, further facilitates this function. Restoration of the original shape of the endodontic instrument has been thought to be of paramount importance during root canal preparation, whereby the restoring force can be pitted against the balancing force as described by Roane et al (1985). However, research by the inventor of this disclosure has indicated that it is this precise function that prevents the instruments from contacting an entirety of the root canal walls, leaving as much as 35% of the internal anatomy of the canal untouched and the preparation poorly centered.

In addition, the continuous contact of the flutes of the endodontic instrument with the canals walls of the canal and the concomitant binding of the instrument, predisposes the instruments to cyclic fatigue and subsequent instrument failure and breakage.

An alternative approach to traditional instruments designed with a coincident center of rotation and center of mass are instruments that have an "off-set" cross-sectional center of mass from the center or axis of rotation. These instruments have been described as swaggering endodontic instruments (e.g., see U.S. Pat. Nos. 8,454,361, 8,882,504, and 8,932,056), but such instruments may also be defined as instruments that cut with a precessional axis.

In some embodiments, when the center of mass of the cross-sectional area of an endodontic instrument is sufficiently off-set from the instrument's axis of rotation, and the vector for centripetal force overtakes the spring constant, the cutting motion is no longer linearly, but helically producing a transverse mechanical wave. These have been termed swaggering endodontic instruments, which will cut precessionally. As with any wave traveling through a medium, a crest is seen moving from point to point. This crest is followed by a trough, which is in turn is followed by the next crest. In the case of a swaggering endodontic instrument, these waves are necessarily created by a disturbance or excitation force, which is usually produced by a dental hand piece. The mechanism by which a wave propagates itself through the metal of the endodontic instrument involves particle interaction, whereby one particle applies a push or pull on an adjacent particle, causing a displacement of the adjacent particle and its dislocation from rest. For the purpose of this disclosure, this can be termed "bodily movement" of the endodontic instrument, and can be reproduced and videoed experimentally. Bodily movement can be engendered using several design nuances, previously described in earlier patent applications and grants (see above).

In some embodiments provided herein, a transverse or cyclical wave pattern can be engendered by grinding or "inscribing" the precessional axis into the metal of the endodontic instrument itself. The wave pattern here is similar, but bodily movement (i.e., instrument displacement owing to deflection) of the endodontic instrument may be absent. As with any wave traveling through a medium, a crest is seen moving along from point to point. This crest is followed by a trough, which is in turn is followed by the next crest. There are many wave patterns that can be identified in nature. The wave pattern relevant here are transverse or mechanical waves exclusively.

An example of a transverse or mechanical wave can be seen manipulating a skip rope. If one ties the loose end of a long rope to a stationary point, stretches the rope out horizontally, and then gives the end being held an up-and-down transverse motion, which can be called the excitation force (Fe), the result is a continuous wave pulse that travels along the length of the rope to its tied end. Observation shows that the pulse travels with a definite speed, maintaining its shape as it travels, and that the individual segments making up the rope move back and forth in a direction perpendicular to the rope's equilibrium position. In physics, this principle can be derived mathematically from the formula $y=f(x, t)$. Here, the equilibrium position is selected along the x-axis (corresponding to the stretched rope), and the transverse or perpendicular displacement is selected along the y-axis, which is the maximum displacement of the rope, or amplitude. Thus, y is a function of both x (the undisplaced position of the point) and time t. This is called the wave function.

At any time t, if one takes a picture of the instantaneous shape of the rope, it will be observed that y varies sinusoidally with x. FIG. 1 depicts a transverse wave which consists of oscillations occurring perpendicular or at right angles to the direction of the wave. The waves are composed of crests and troughs with a specific amplitude that determines the energy or force transmitted by each wave.

In the first application, once an upwards and downwards excitation force is introduced into the rope, the particles of the rope also begin to oscillate upwards and downwards. At any given moment in time, a particle on the rope could be above or below the rest position. Points A, E and H on the transverse wave represent maximum amount of positive or upward displacement from the rest position. The troughs of a wave C and J are the points on the transverse wave which exhibits the maximum amount of negative or downwards displacement from the rest position.

Figure 2A:
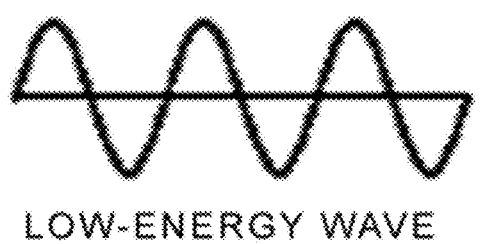
FIG. 2A depicts an example low-energy wave pattern.
Figure 2B:
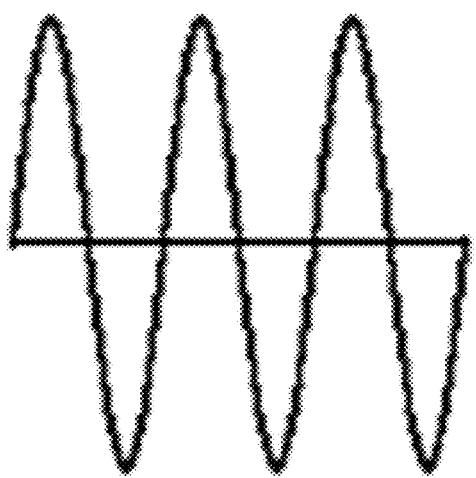
FIG. 2B depicts an example high-energy wave pattern.

The amount of energy carried by a wave is related to the amplitude of the wave. Putting more energy into a transverse pulse will not affect the wavelength, the frequency or the speed of the pulse. The energy imparted to a pulse will only affect the amplitude of that pulse. The more energy imparted to the wave, the higher will be the corresponding amplitude as illustrated by a comparison of the waves of FIGS. 2A and 2B. Conversely, lesser values of imparted energy produce smaller amplitudes.

With regard to endodontic instruments that have a precessional axis is ground into the body of the endodontic instrument, the forgoing wave principles owing to physical deflection do not necessary apply in all cases, but may apply in some cases.

Precessional Cutting

Figure 3:
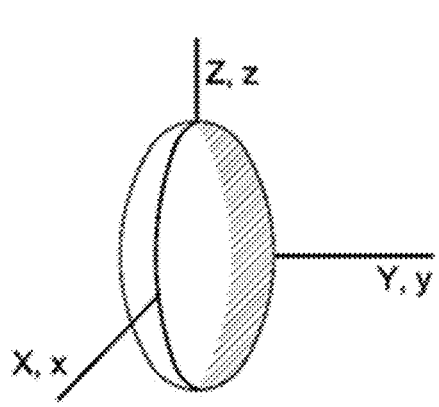
FIG. 3 depicts an object in an initial position.
Figure 4:
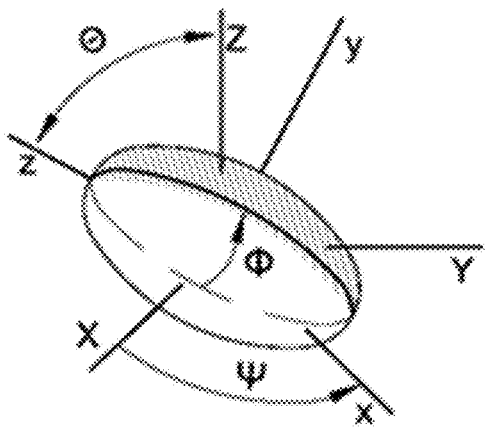
FIG. 4 depicts the object of FIG. 3 in rotation.

In order to better understand endodontic instruments that cut precessional, some brief background into geometry and mathematics is now provided. Eulerian angles are a set of angles used to describe the orientation of any object relative to a coordinate system. In order to develop these angles, it is assumed that an object has an axis of rotational symmetry and two reference frames: a secondary coordinate system xyz, whose z-axis is coincident with the object's axis of symmetry, and an inertial primary coordinate system XYZ. FIG. 3 shows the object in an initial position. The body is then put through a series of rotations to establish the Eulerian angles as shown in FIG. 4. The angles ψ and Θ specify the orientation of the secondary xyz system relative to the primary XYZ system. Ψ (psi) is called the precession angle and Θ (theta) is called the nutation angle. The angle φ (phi) specifies the rotation of the rigid body relative to the xyz system and is called the spin angle. These three angles are called the Eulerian angles. The precession rate is the rate at which the xyz system rotates about the Z-axis, the precession axis.

Figure 5:
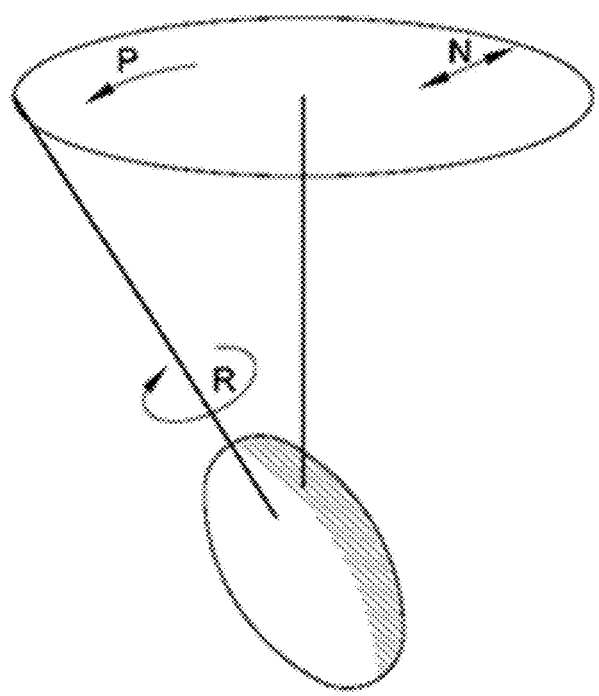
FIG. 5 depicts the object of FIG. 3 in precessional motion.

The Eulerian angles can then be used to develop equations of angular motion which describe mathematically the behavior of a rotating body in precession. The scope of the mathematics is complex and does not need to be addressed here, however, a general idea of the resulting motion of a body in precession is provided in FIG. 5. The body is rotating about its own axis, shown as R, while simultaneously rotating (precessing) about the central axis P. N represents the nutation of the body, which is a rocking or oscillation of the body itself as it precesses about the central axis, which can be considered negligible in this case.

Figure 6A:
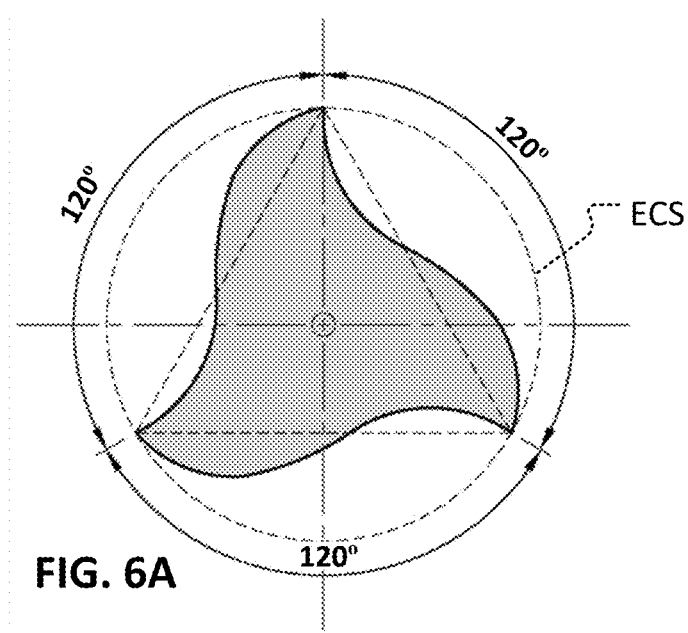
FIGS. 6A-6C depict cross-sectional views of the endodontic instrument of FIG. 6 at cutting-plane lines A-A, B-B, and C-C respectively.
Figure 6B:
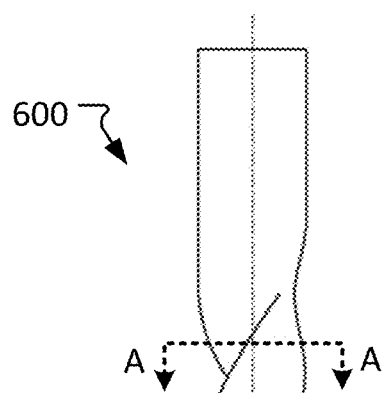
Figure 6B:
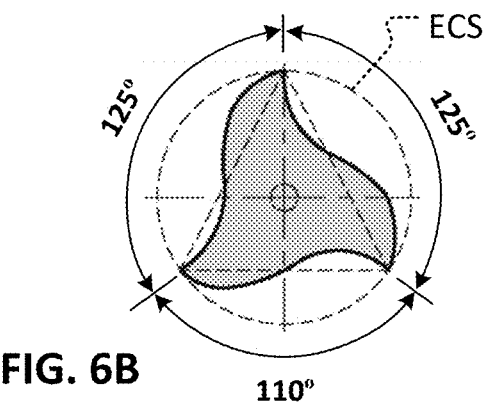
Figure 6C:
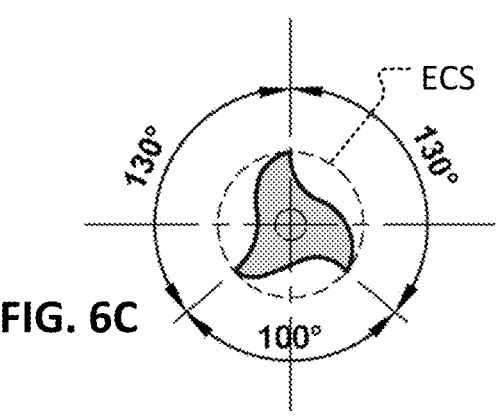
Figure 6:
FIG. 6 depicts an example endodontic instrument.
Figure 6:

As mentioned above, endodontic instruments that precess by off-setting the center of mass of the endodontic instrument from the center of rotation can be created in various ways. There are at least two fabrication methods that can be used to achieve this result. A first such fabrication method ("method 1") shifts the center of mass from the central axis, continuously, along its length using asymmetric cross-sections. An example of method 1 is shown by example endodontic instrument 600 in FIG. 6. In method 1, the endodontic instrument (e.g., endodontic instrument 600) is ground linearly along the central axis, but the cross section of the endodontic instruments varies asymmetrically along the length of the central axis. For example, in the depicted example the cross-sectional shape of endodontic instrument 600 is an equilateral triangle at cross-section A-A (FIG. 6A), and the cross-sectional shape increasingly becomes an isosceles triangle along the body of the instrument in the direction toward the tip (see FIGS. 6B and 6C). This same concept can be applied utilizing instruments with other asymmetric cross-sections, for example a trapezoidal cross-section. In these examples, bodily movement (from material deflection) is a function of the asymmetry and centripetal force, which defines the precession angle.

In a second fabrication method ("method 2") by which endodontic instruments can be made to operate using precessional motion, the cross-section of the endodontic instrument is symmetrical or bi-symmetrical and ground such that the center of mass of the cross-section is off-set at a distance away from the rotational axis. The off-set cross-section revolves around the central or rotational axis as it is being ground.

Figure 7A:
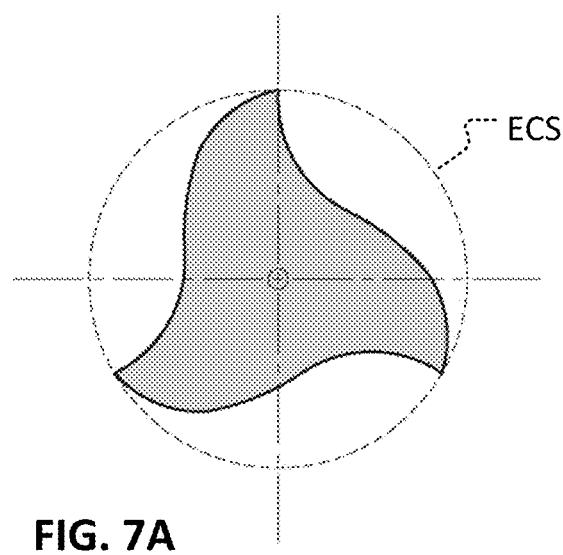
FIGS. 7A-7C depict cross-sectional views of the endodontic instrument of FIG. 7 at cutting-plane lines A-A, B-B, and C-C respectively.
Figure 7B:
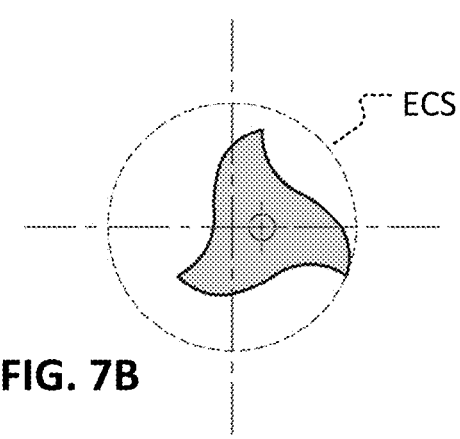
Figure 7C:
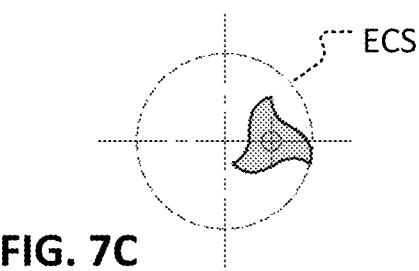
Figure 7:
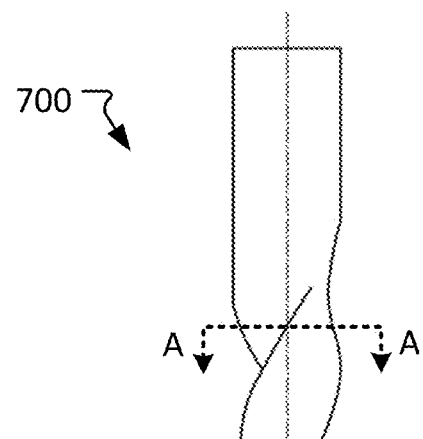
FIG. 7 depicts another example endodontic instrument.
Figure 8A:
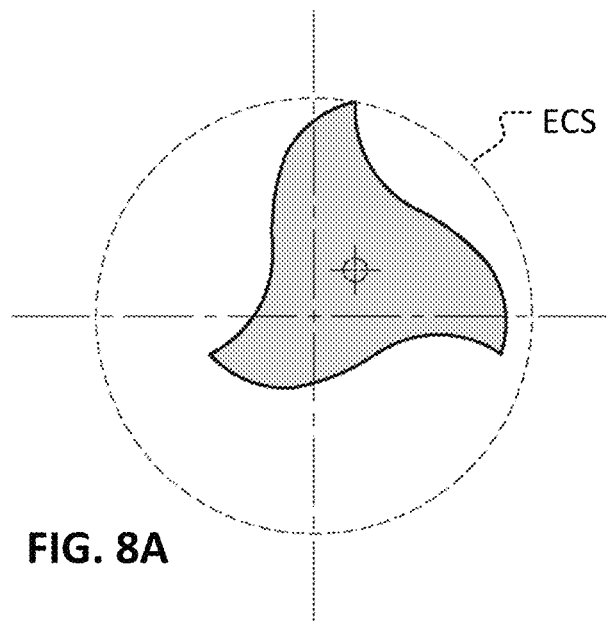
FIGS. 8A-8C depict cross-sectional views of the endodontic instrument of FIG. 8 at cutting-plane lines A-A, B-B, and C-C respectively.
Figure 8B:
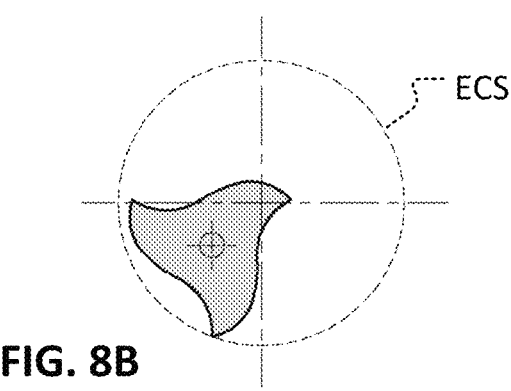
Figure 8C:
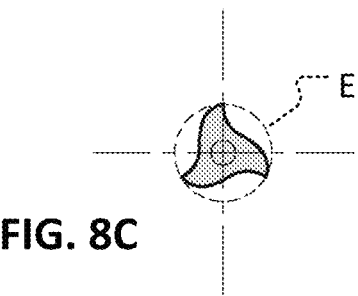
Figure 8:
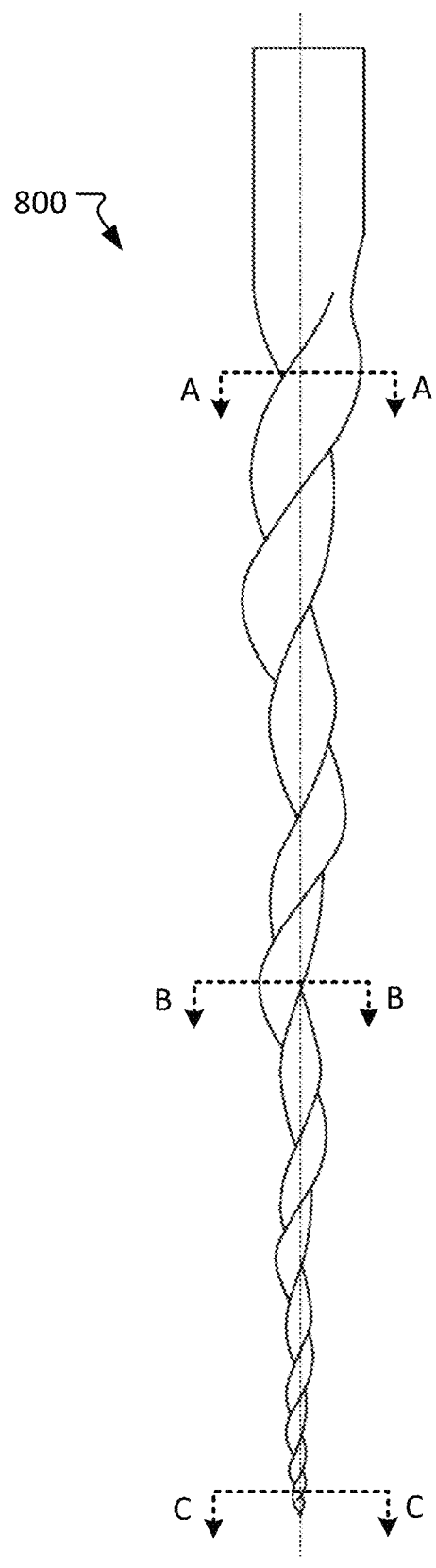
FIG. 8 depicts another example endodontic instrument.

As can be seen from FIGS. 7 and 8, for example, the distance between the centers of mass (centroids) of the cross-sections (which are off-set from the axis of rotation, or "offset" for simplicity) and the central axis of rotation varies along the length of the endodontic instrument. This offset distance may increase or decrease monotonously or can accelerate. Further, the offset can originate from the shank and extend progressively farther away from the central axis from the shank to the tip as depicted by endodontic instrument 700 (FIG. 7), or originate at the tip and extend progressively farther away from the central axis from the tip to the shank as depicted by endodontic instrument 800 (FIG. 8).

Figure 9A:
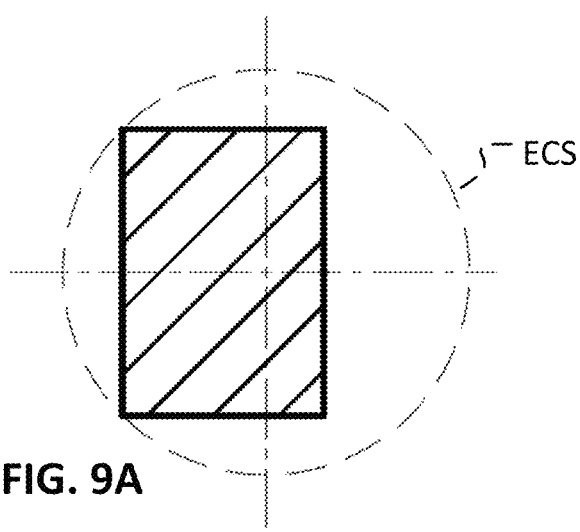
FIGS. 9A-9D depict cross-sectional views of the endodontic instrument of FIG. 9 at cutting-plane lines A-A, B-B, C-C, and D-D respectively.
Figure 9B:
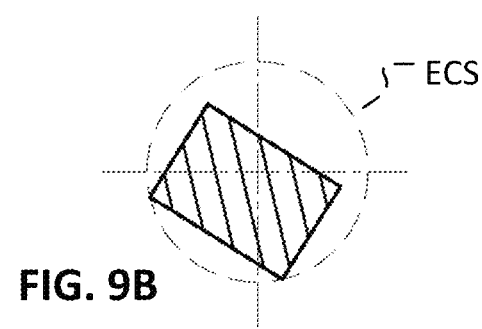
Figure 9C:
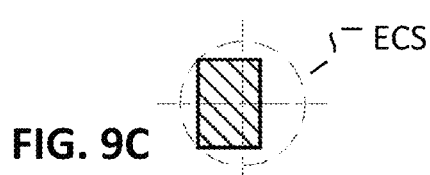
Figure 9D:
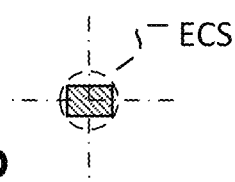
Figure 9:
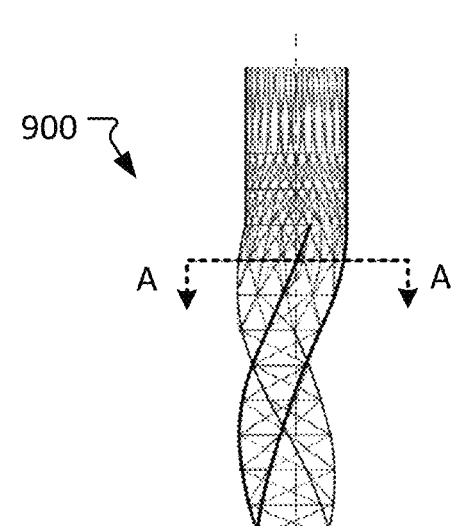
FIG. 9 depicts another example endodontic instrument.
Figure 9:
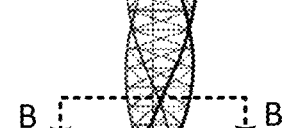
Figure 9:
Figure 9:

FIG. 9 illustrates an example endodontic instrument 900 that has offset rectilinear cross sections (except at the tip where the cross-section in centered on the axis of rotation). For example, as shown in FIG. 9A, even the center of mass of the cross-section at the shank end of the working body of the instrument 900 is offset from the axis of rotation.

When the center of mass of the cross-section is offset from the axis of rotation, one or more of the edges of the instrument are out of contact with the wall of the ECS. For example, as shown in the examples of FIGS. 9A-9C, only two edges of the rectilinear cross-section engage the walls of the root canal at any one time. This offset rectilinear cross-section not only contributes to the innate flexibility of the endodontic instrument 900, but also permits intermittent cutting, which mitigates cyclic fatigue. The large clearance angle opposite the cutting flutes facilitate hauling and elimination of debris Example endodontic instrument 900 (which is configured using method 2 and depicted in wire-form in FIG. 9) has a cutting axis that is different than the rotational or central axis. The cutting axis is inscribed in (ground in) the instrument 900 by off-setting a rectilinear cross-section (in this example) from shank to tip. Again, the symmetrical, or in this case bi-symmetrical cross-section, can be seen revolving around the central axis, deploying only two cutting edges. In result, the path defined by the centers of mass of the cross-sections spiral around the axis of rotation of the instrument 900. The offset starts at the shank end of the working body (as shown in FIG. 9A) and become progressively less along the working body in a direction towards the tip. At the tip, the center of mass of the cross-section is coincident with the axis of rotation (as shown in FIG. 9D).

An instrument design using this configuration will precess in both the x-axis and the y-axis, similar to the asymmetric cross-section, without necessarily displaying any bodily deflection. An offset rectilinear cross section such as this, can contribute to the innate flexibility of the endodontic instrument 900, while permitting intermittent cutting, which will mitigate cyclic fatigue. In addition, the larger clearance angles opposite the cutting flutes will facilitate hauling and elimination of debris, further improving the resistance to cyclic fatigue.

Figure 10B:
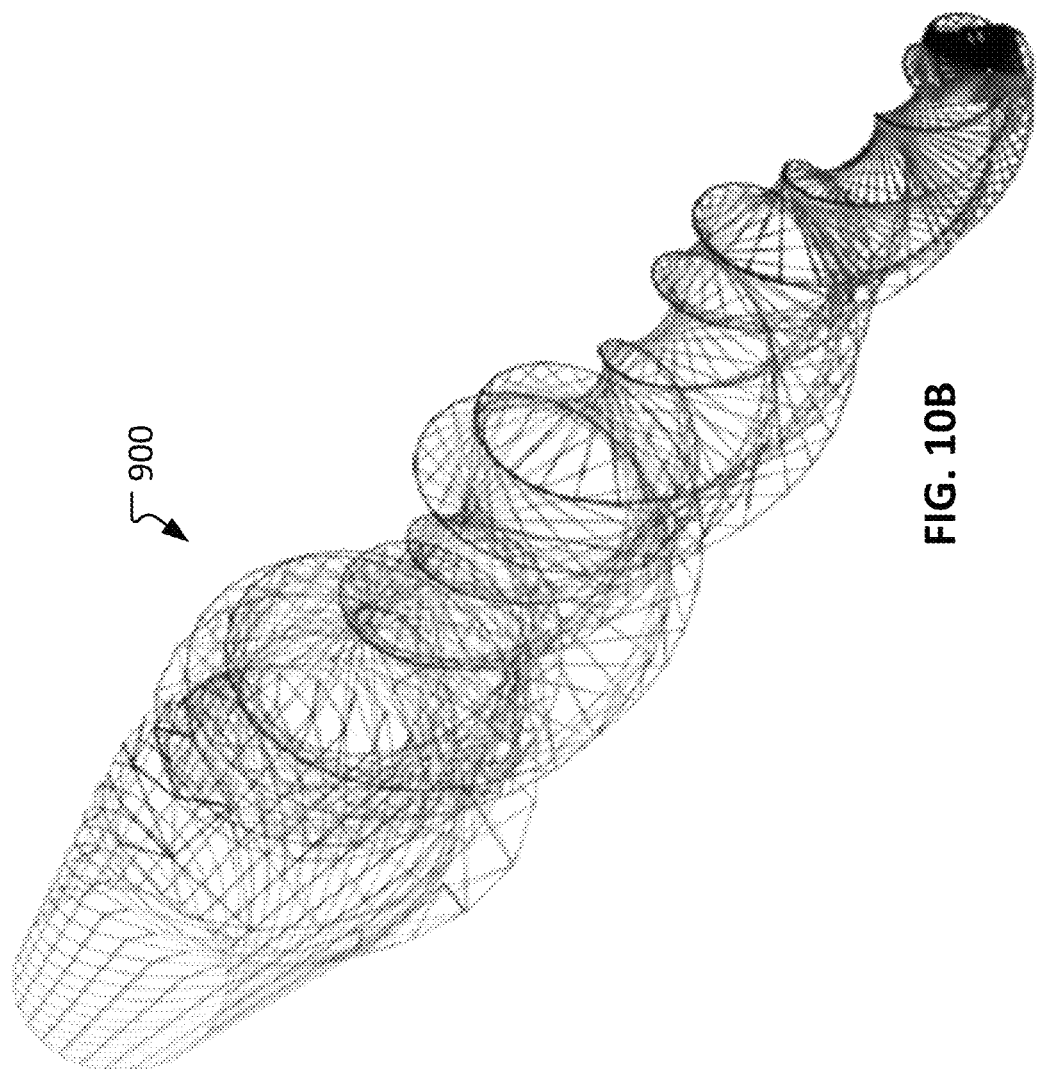
FIGS. 10A and 10B are perspective wire-frame illustrations of the endodontic instrument of FIG. 9.
Figure 10A:
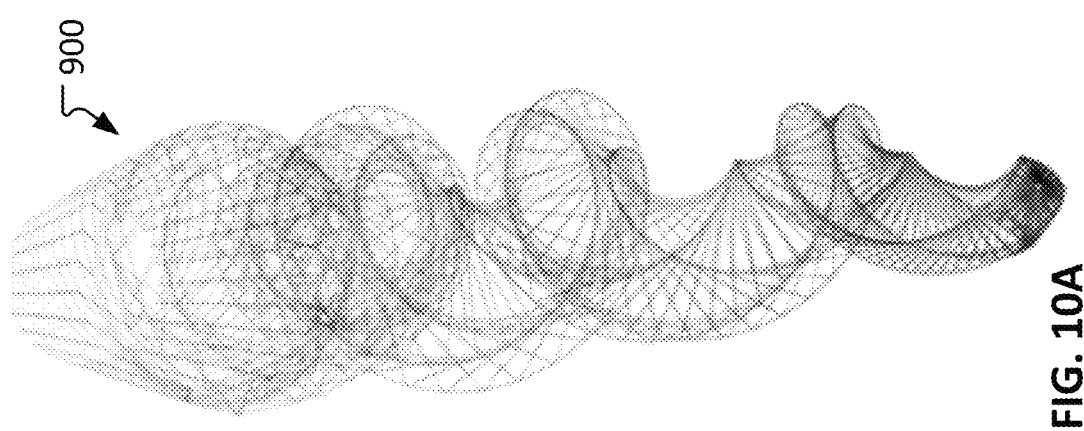

FIGS. 10A and B are perspective images of the endodontic instrument 900 demonstrating the spring or coil-like configuration of the instrument. In addition, when the cross-section is off-set at a significant or "threshold distance" away from the central axis, as shown in FIGS. 10A and 10B, one can visualization of the diametrical "compressibility" of the endodontic instruments (such as endodontic instrument 900 and other instruments described herein), which will be described further below.

Again, and as depicted by the example endodontic instrument 1110 in FIGS. 11A and 11B, the design and fabrication method 2 (i.e., grinding the instrument such that the centers of mass of the cross-sections are offset from the axis of rotation), results in the cutting axis (also referred to herein as the "center of mass path") being offset from the axis of rotation of the endodontic instrument while the instrument is in a natural condition (i.e., free from external stresses).

In this example, the center of mass path 1141 spirals around the axis of rotation 1140. When viewed in 3-dimensions, Axis 2 also becomes a precessional axis. The amount of off-set between the center of rotation and the center of mass is defined by the distance 1147 between these two axes 1140 and 1141, and varies along the entire length of the endodontic instrument 1110. In this particular example, the distance 1147 is maximum at the shank end (where the working body joins the shank) and gradually reduces along the working body (to zero at the tip, i.e., the tip is completely centered).

In further consideration of the endodontic instrument constructed according to method 2, the precessional axis also produces a transverse mechanical wave defined by a series of peaks and troughs. The amplitude or heights of the peaks are at a maximum when the endodontic instrument is in its free and unconstrained position. When the endodontic instrument is inserted into the root canal, the peaks may be compressed. The amount of compression will depend upon the diameter and the curvature of the canal (ECS). Theoretically, when the endodontic instrument is fully compressed, the center of mass path 1141 will flatten out and be collinear with the axis of rotation 1140. As each peak along the endodontic instrument is elastically compressed, it behaves like a small spring and is a source of potential or stored energy.

Analysis of Endodontic Instruments as a Variable Rate Spring

Another factor that must be considered in understanding the function and advantages of the endodontic instrument made in accordance with method 2, is studying the endodontic instrument's stiffness and/or flexibility. As clearly seen in the perspective views of FIGS. 10A and 10B, such endodontic instruments possess the unique configuration of a coil or spring which differentiates it from traditional endodontic instruments.

Stiffness and/or flexibility can be quantified using a parameter known as a spring constant ("k"), which is defined as the amount of force that is required to cause a unit of deformation. In its general form, $k=F/\delta$, where k equals the stiffness, F equals force and $\delta$ equals displacement. Equations for the determination of the spring constant of actual mechanical systems are widely available in engineering literature. Due to the constantly changing cross section of an endodontic instrument of the designs described herein, the spring constant of the endodontic instruments will vary along their lengths. This spring constant, together with the endodontic instrument precession, directly affects the cutting forces applied to the surrounding root dentine during cutting.

In the first part of this analysis, the spring condition along the entire length of the endodontic instrument will be considered. In the offset tip endodontic instrument design (e.g., as shown in FIG. 7), the tip of the endodontic instrument is in its unconstrained condition and sits at some distance from the central axis. The offset shank design (e.g., FIGS. 8, 9, and 11) reverses the direction of the offset angle. The following discussion is applicable to both the offset tip and the offset shank designs.

Figure 12A:
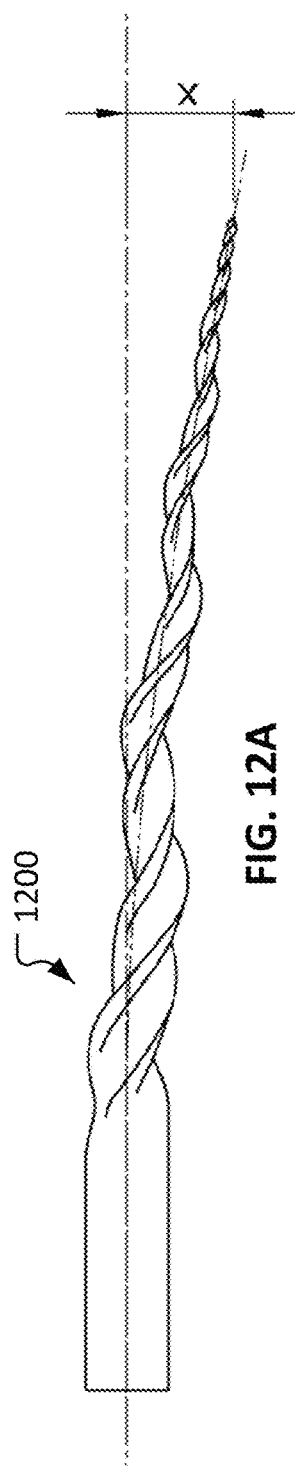
FIG. 12A depicts an example endodontic instrument with a tip that is offset from the axis of rotation.
Figure 12B:
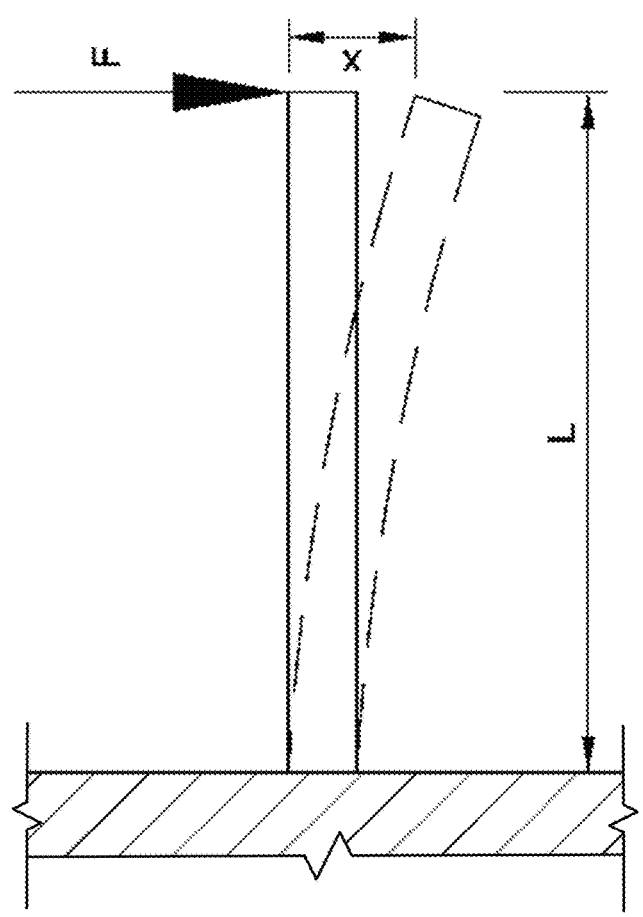
FIG. 12B depicts a cantilevered beam that is deflected by a force.

FIG. 12A depicts an endodontic instrument 1200 with offset tip, which can be analyzed in general terms using the equations for a cantilevered beam as depicted in FIG. 12B.

In FIG. 12A, an example endodontic instrument 1200 with offset tip design in its unconstrained condition is shown. If this endodontic instrument 1200 is inserted into a relatively straight endodontic cavity with a diameter that is narrower than the diameter of the endodontic instrument's cutting envelop, the endodontic instrument 1200 will be constrained along its length such that its axis of rotation and the central axis become more closely aligned. The resulting condition can be analyzed in general terms using the equations for a cantilever beam as depicted in FIG. 12B. As the endodontic instrument 1200 is rotated, the constrained or compressed endodontic instrument will expand and the coil-like structure will try to return to its unconstrained position. The ability of the endodontic instrument to return to the unconstrained position will be dependent upon its stiffness k, but also on the distance x (FIG. 12B) as seen in the equation F=kx. Thus, the greater the distance of the off-set cross-section from the central axis the greater the "stored energy" which can translate into passive cutting during rotation. As previously mentioned, this feature would not only serve to accommodate the endodontic instrument 1200 as it passes into and through a narrow or tortuous portion of the root canal, but would also serve to mitigate the opportunity for cyclic fatigue.

Figure 13A:
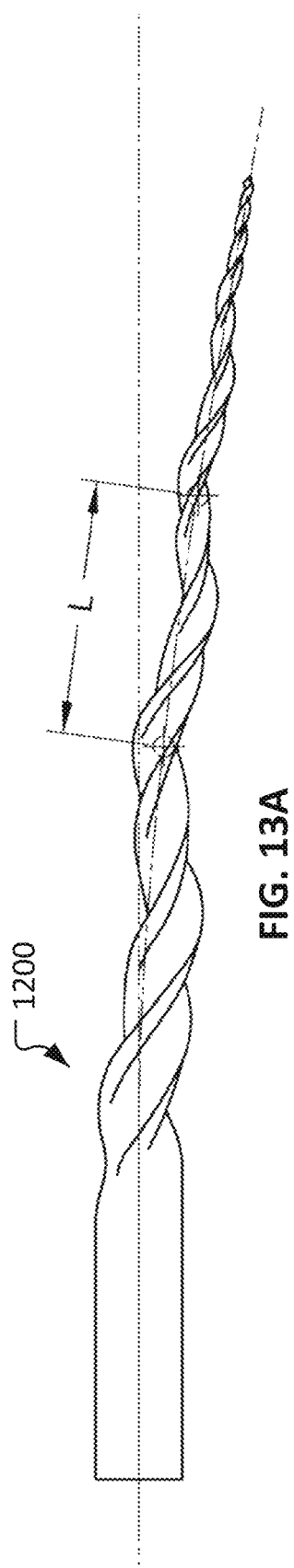
FIG. 13A depicts an example endodontic instrument with a tip that is offset from the axis of rotation.
Figure 13B:
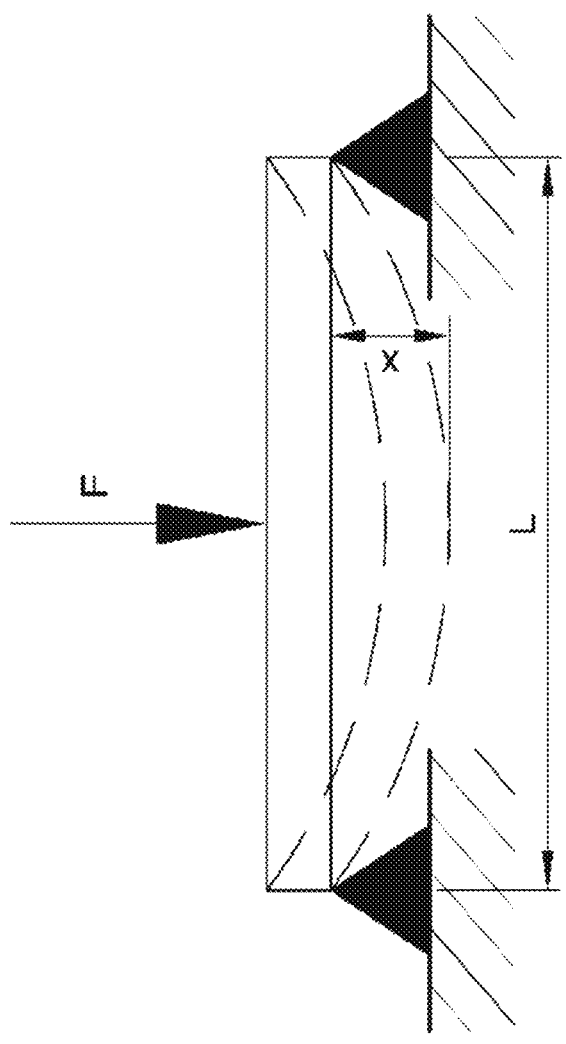
FIG. 13B depicts a simply supported beam that is deflected by a force.

FIGS. 13A and 13B can be used to analyze a localized section L of the endodontic instrument 1200 as it bends to conform to the ECS during use. L is distance between the crest of two nodes, with which the spring rate of a single wave between the crests can be analyzed. FIG. 13B is a schematic of a simply supported beam where x is the maximum deflection, If the localized section L of the endodontic instrument is analyzed using the terminology defined in the waveform discussion above, the spring rate k of a single wave crest between two nodes can be analyzed. In this case, the localized performance of the endodontic instrument can be analyzed using the equations for a simply supported beam in $FL^3/48EI=48EI/L^3$. L represents the distance between any two nodes, "I" represents the moment of inertia which is dependent upon the cross sectional area of the endodontic instrument and will vary along its length, and "E" represents the modulus of elasticity (Young's Modulus), which is used to define the stiffness of different materials.

When the initial conditions of this endodontic instrument 1200 as it is inserted into an ECS and undergoing radial constraining forces are evaluated, the reverse occurs of what is depicted in FIGS. 12A and 13A, that is, the instrument shown is those figures is in its unconstrained or uncompressed condition. Here F represents the force exerted on the endodontic instrument by the canal wall. Since the endodontic instrument is built with multiple nodes (crests ad troughs) and potential deflections, the tendency of F will be to straighten out the endodontic instrument along its length. When the endodontic instrument is fully constrained, x, which represents the deflection of the endodontic instrument due to F would be zero (or nearly zero) and the cross-section of the endodontic instrument will be completely centered.

Figure 14B:
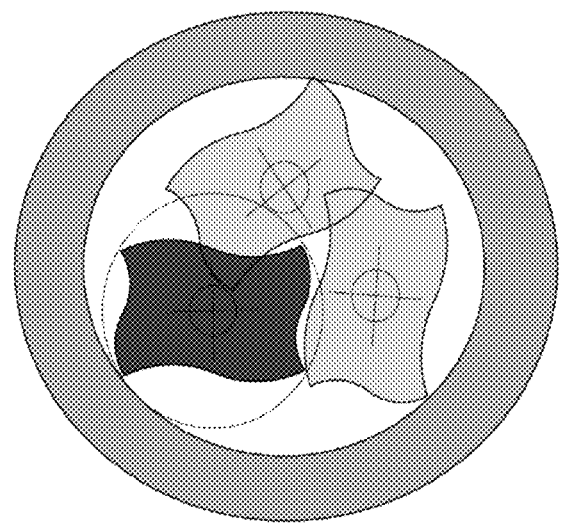
FIG. 14B illustrates the tendency of the endodontic instrument of FIG. 14A to seek its natural configuration when diametrical constraints are reduced.
Figure 14A:
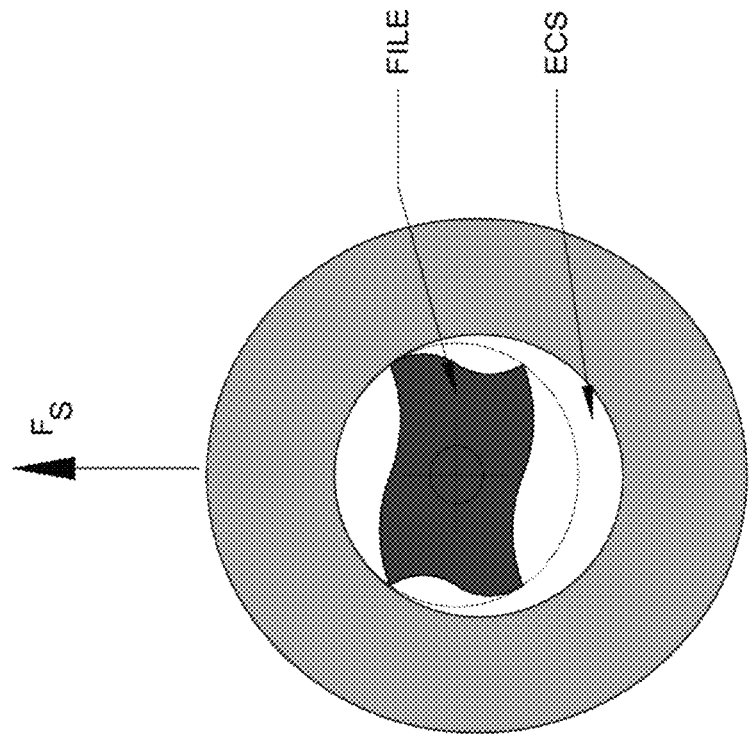
FIG. 14A illustrates a cross-section of an example endodontic instrument in a constrained condition within an endodontic cavity space.
Figure 15B:
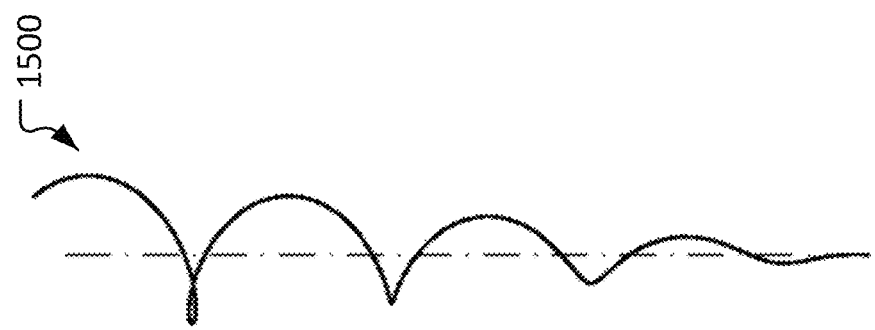
FIGS. 15A-15F are schematic illustrations of an endodontic instrument as it transitions from an unconstrained condition to a completely constrained condition.
Figure 15A:
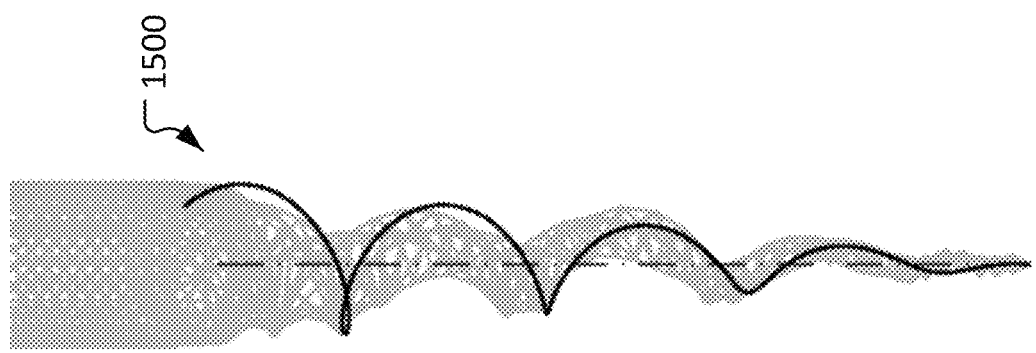
Figure 15D:
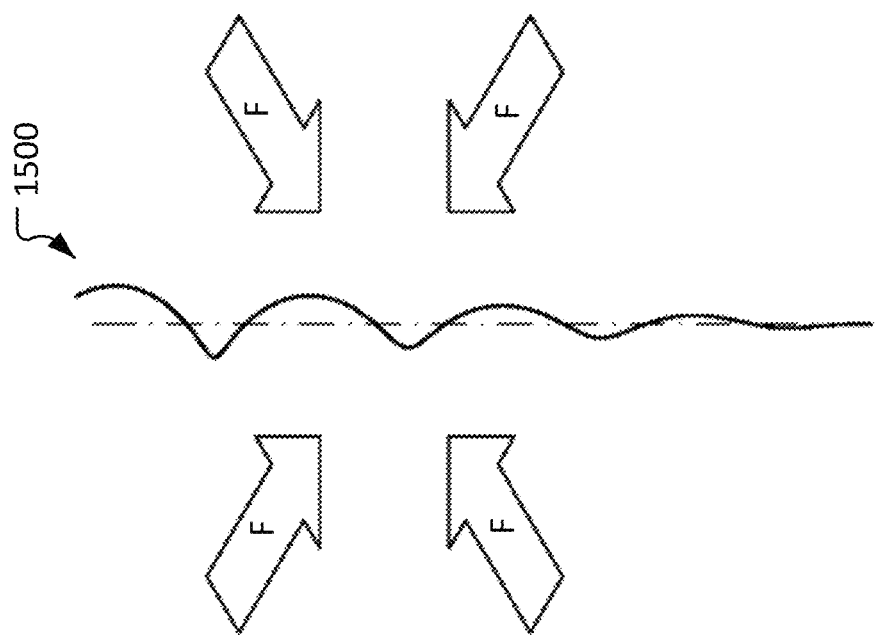
Figure 15C:
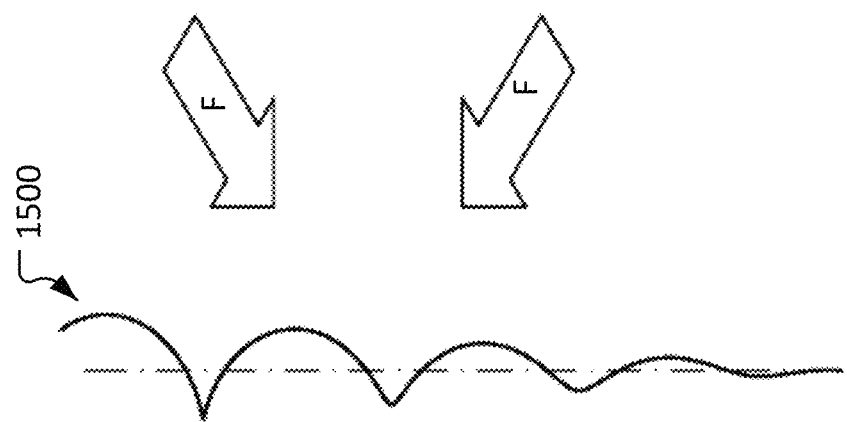
Figure 15F:
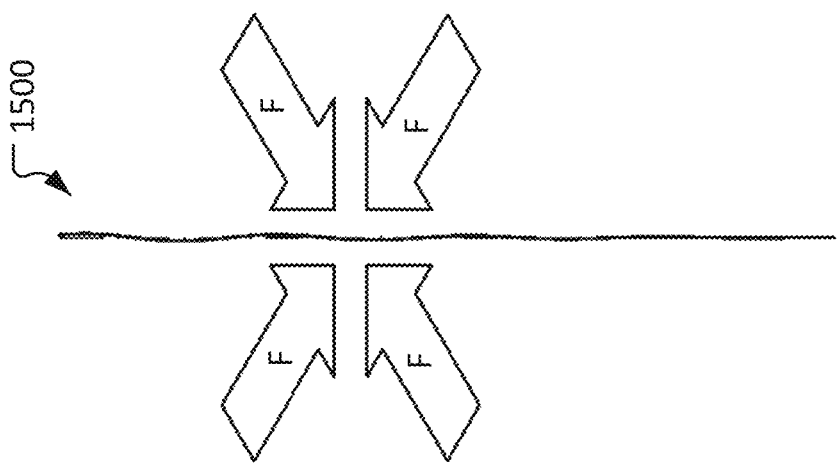
Figure 15E:
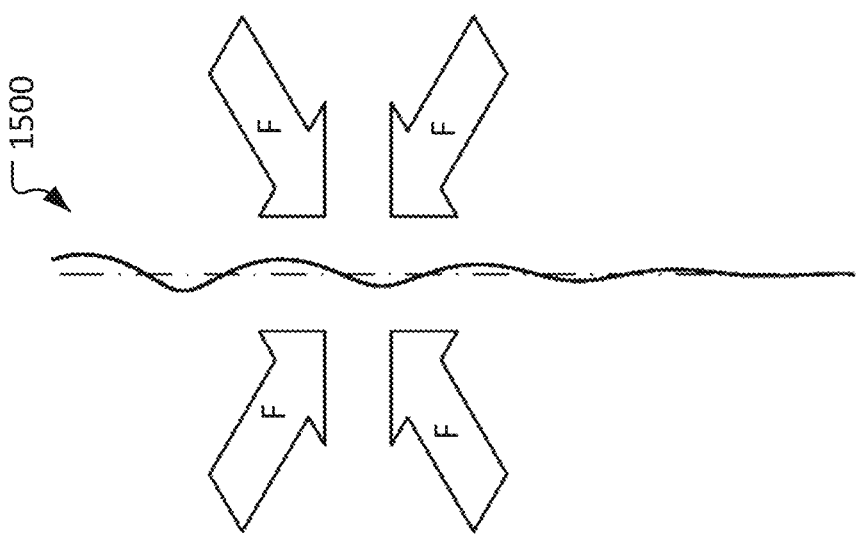

FIG. 14A depicts the cross-section of the instrument when in its constrained or compressed condition. When the endodontic instrument is fully constrained, x, which represents the deflection of the endodontic instrument due to F, would be zero or nearly zero.

FIG. 14B demonstrates the endodontic instrument's inherent tendency to return to its natural or less-compressed state in which it is precessing about its central axis.

An overview and schematic of an example spiral instrument 1500 in its entirety, as it transitions from its initial unconstrained condition to a completely constrained condition is shown in FIGS. 15A through 15F. In its completely unconstrained state (FIGS. 15A and B), the instrument 1500 presents as a spiral or coil-like structure, which is compressible as described above.

Lateral forces F, depicted by the arrows in FIGS. 15C-15F are generated as the endodontic instrument is inserted into the ECS, which is in this example radially narrower than the outer profile of the instrument 1500. When the endodontic instrument 1500 is completely constrained and x (the distance between the cross-sectional centers of mass and the axis of rotation) is zero, the endodontic instrument becomes straight or nearly straight as show in FIG. 15F. As the endodontic instrument 1500 rotates, the cutting edges under the load of the spring force, will begin to remove material from the surrounding cavity. This process will continue until the endodontic instrument 1500 has enlarged the ECS based the endodontic instrument 1500 diameter and the precessional axis. In this final unconstrained condition, the spring force or cutting force will be nearly zero and the endodontic instrument 1500 will be rotating freely about the central axis.

A design of this nature, would theoretically allow the instrument 1500 to engage the walls of the ECS intermittently as the constrained coil rotates in the canal and allowed to unwind releasing "stored energy". As already eluded to, the release of stored energy is dissipated gradually, which would minimize binding, mitigate cyclic fatigue, and provide the opportunity to clean both inner and outer curvature of the canal wall more thoroughly.

This phenomenon of diametric compressibility can also facilitate the negotiation of more complicated anatomy, i.e., enable better maneuverability in narrowing or constricted and tortuous ECS architecture. In addition, endodontic instruments such as these are more compliant and will demonstrate better centering and less apical transportation, which will better preserve the original anatomy of the ECS.

Mass Moment of Inertia

When studying the performance of an endodontic instrument body, reamer, or a drill during cutting, one consideration is the moment of inertia of the cross-section, which is a measure of its resistance to distortion and torsional failure.

When the cross-sections of various endodontic instruments are examined, it can be discovered that a rectangular cross-section, has innate advantages over a triangular cross-section. Also the reason why orientation of the cutting blades (edges) in the long axis of the cross-section is advantageous can be discovered.

Comparing the formulas for moment of inertia for both a triangle ($I_{triangle}=bh^3/36$) and a rectangle ($I_{rectangle}=bh^3/12$), it can be seen that the inertia for a rectangle is at least ⅓ greater than that of a triangle with similar base and height.

Another consideration is the resistance of the cross-section to flexural failure or torsional failure. In planar physics, and as just mentioned, the moment of inertia is the capacity of a cross-section of a mass to resist distortion. It is considered with respect to a reference axis and how that cross-sectional area is distributed about the reference axis, usually a centroidal axis. The moment of inertia (also described as the second moment of the area) is expressed in its simplest mathematically terms as:

$$I_x=\Sigma(A)(y^2)$$

"A" is the area of the plane of the cross-section and "y" is the distance between the centroid of the object and the central or x-axis. In further considering an endodontic instrument, and in particular an endodontic instrument with rectilinear cross-section, it can be readily seen the displacement of the centroid of the cross-section plays a much more important role than the area of cross-section itself in resisting distortion. As seen from the formula above, improvements in the torsional inertia of a planar object increases, not only by the area the object, but by the square of the distance between the turning (central axis) and the centroid (center of mass).

On further analysis, it can be seen that improvement of the mass moment of inertia, which is related to the planar moment of inertia, can also improve resistance to distortion. This is best described by the parallel-axis theorem and in the context of FIG. 16A, where a lamina or cross-section of an offset cylindrical drill body with a rectilinear cross-section is seen.

Figure 16A:
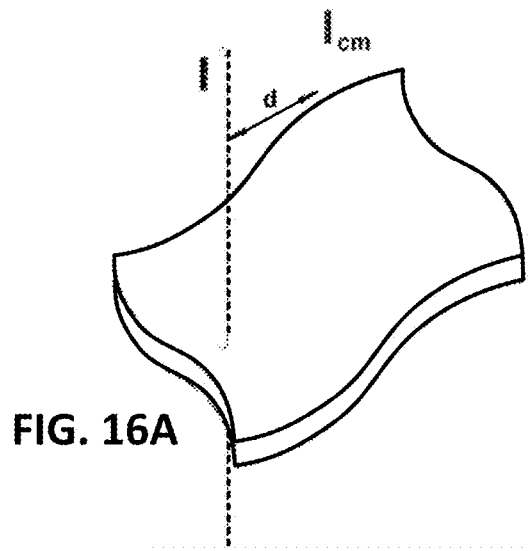
FIG. 16A is a free body diagram demonstrating the components of a lamina of an example endodontic instrument with an offset center of mass.

FIG. 16A is a schematic demonstrating the components of a lamina of an endodontic instrument with an offset center of mass and the components under consideration in applying the parallel axis theorem.

Referring to FIG. 16A, one can write the formula for the parallel-axis theorem as:

$$I=I_{cm}+md^2$$

Here "$I_{cm}$" is the moment of inertia of a body of mass "m" with respect to a line through its centroid "cm." "I" is the total moment of inertia with respect to a line parallel to the central axis or axis of rotation, and "d" is the distance between the two lines. Thus, for a given lamina, total inertia I (and the resistance to distortion) can be improved by improvements in both the mass of a cross-section and an exponential increase in the distance from the central axis to the centroid.

A practical example of the parallel-axis theorem is a hammer rotating about an axis perpendicular to the handle. The farther the axis of rotation extends away from the head of the hammer, and toward the end of the handle, the greater the total inertia at the end of the hammer after it is released, rotates and strikes an opposing surface.

Figure 16B:
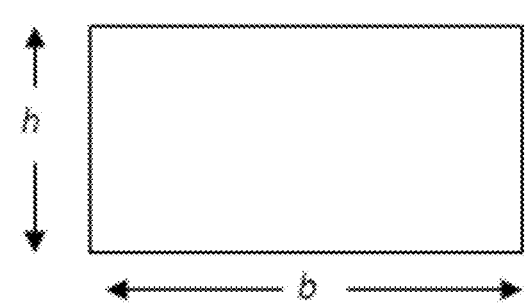
FIG. 16B illustrates a cross-sectional view of an example endodontic instrument that has a rectilinear shape.

In the case of an endodontic instrument with a rectangular cross-section, it is helpful to understand that the moment of inertia (or the resistance to distortion) is continually varying as the instrument rotates. The cross sectional view of this endodontic instrument can be simplified such that it can be looked at as a two-dimensional rectangle or any quadrangle (see FIG. 16B).

Two different values for the moment of inertia can be calculated using the equation:

$$I_x = bh^3/12$$

In one instance, b will be along the long axis of the rectangle (and the cutting axis) and in the second instance b will be represented by the shorter axis, the bending axis. The moment of inertia when b is along the shorter axis will be much less, which dictates this as the bending axis.

As an endodontic instrument with a rectangular cross-section rotates and enters a curved ECS, it will be continuously alternating between its two moments of inertia (between stiff and flexible positions). Due to lower stress on the endodontic instrument that is associated with the thinner cross section (smaller moment), the endodontic instrument will naturally tend to bend around this axis as it rounds the curve of a canal, but continually oriented such that the cutting blades remain in the long axis for maximum strength or resistance to distortion.

Thus, the geometry of the cross-section of this endodontic instrument has been optimized to provide the best endodontic instrument performance. The endodontic instrument is wider and stiffer through one direction of the cross section (providing the strength and rigidity during cutting) and a thinner and more flexible across the other direction of the cross section (for flexibility). The continued rotation of the endodontic instrument allows both of these characteristics to be manifest simultaneously and, of course, influences the endodontic instrument's performance.

Figure 16C:
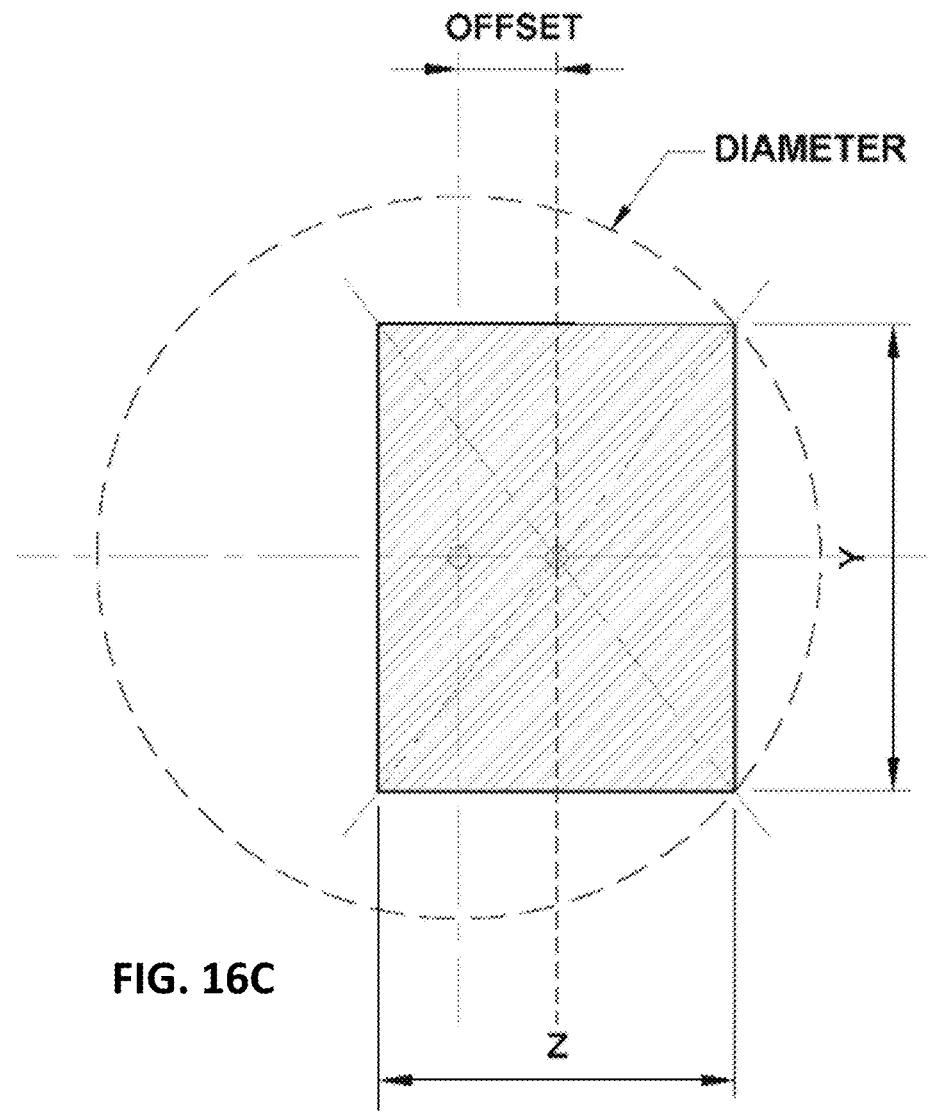
FIG. 16C illustrates a cross-sectional view of an example endodontic instrument that has a rectilinear shape that is offset from a central axis.

FIG. 16C. is a schematic of an offset rectilinear endodontic instrument demonstrating the adjustability of the distance of the offset from central axis. The offset rectilinear cross-section as seen in FIG. 16C demonstrates how the mass of the endodontic instrument can be adjusted across any lamina, improving flexibility and resistance to cyclic fatigue. As can be seen from the diagram, the endodontic instrument can be made more or less resistant to distortion or more or less flexible by increasing or decreasing the distance of the offset from the central axis. Obviously, there is an optimum offset distance and orientation of the cross-section, which offers both resistance to torsional failure and maximum flexibility. This distance, however, is dependent on the configuration of the cross-section of the endodontic instrument itself, the number of nodes of the endodontic instrument, the distance between each node (also called pitch), the diameter of the instrument at any point along its working surface, which is dictated by the tips size and taper (and whether the taper in uniform or variable), the material the endodontic instrument is made from and numerous other variables. It the experience of the inventor, however, that optimization occurs when the centroid is displaced 20% or more from the axis of rotation. Instruments that are ground with this specification have been demonstrated to be compressible between one and two instruments sizes or 0.05 to 0.10 mms when compared to traditional instruments (instruments which a similar rotation axis and centroid) without offset, where the compressibility of traditional instruments is negligible.

FIGS. 17A-17V illustrate an implementation of an example endodontic instrument 1700 described herein. In FIGS. 17A-17G, the endodontic instrument 1700 is shown in its natural shape (unaffected by external forces). In FIGS. 17H-17N, the endodontic instrument 1700 is shown in a radially constrained state.

The endodontic instrument 1700 includes four sides and edges, is rectilinear in transverse cross-section, and can be utilized to remove tissue and/or dentin from an ECS. The instrument 1700 includes a shank 1710 and a working portion 1712, which is tapered in a shank to tip direction. The tip 1713 includes an active or cutting surface, which is confluent with the working surface 1712. Alternatively, the leading tip 1713 can include a non-active or non-cutting surface, which is also confluent with the working surface 1712. The maximum flute diameter (MxFD) 1717 is located near the shank end 1711 of the cutting surface and the minimum flutes diameter (MnFD) 1716 is located near the tip 1713. The shank 1710 above the working portion 1712 is essentially cylindrical and exhibits a slightly larger diameter than the working surface 1712. A fitting, which is suitable for an engine driven motor of a hand-piece and chuck, or a handle utilized for manual instrumentation, can be attached to the shank 1710.

While the endodontic instrument 1700 is in its natural, unconstrained state, the center of mass path 1741 of the endodontic instrument 1700 spirals around the axis of rotation 1740. The offset is maximum where the working surface 1712 meets the shank 1710. From the position where the working surface 1712 meets the shank 1710, proceeding toward the tip 1713, the offset decreases. The offset at the tip 1713 is zero (i.e., the center of mass at the tip 1713 is on the axis of rotation). Hence, the endodontic instrument 1700 in an unconstrained state will have a conical outer profile when rotated about its axis of rotation 1740.

Figure 17O:
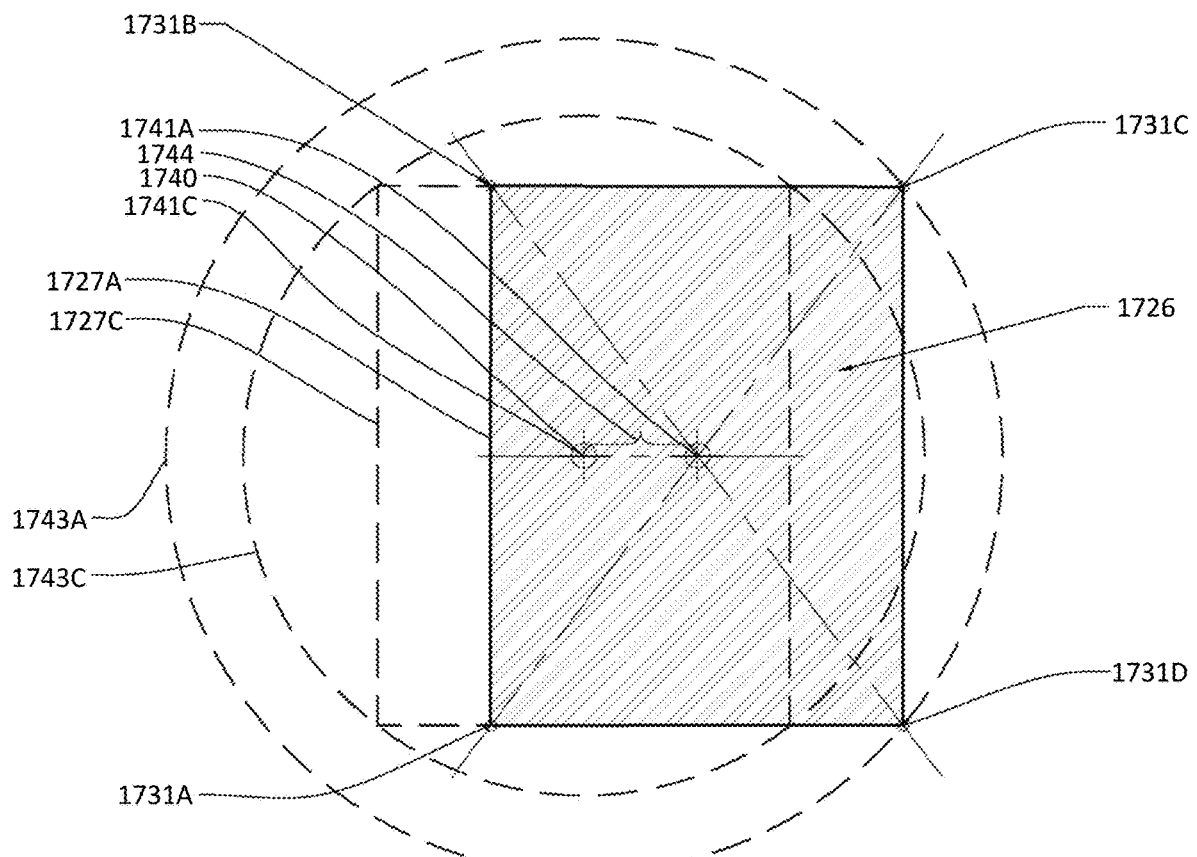
FIG. 17O depicts a cross-section of the instrument of FIGS. 17A and 17B.
Figures 1, 17O:
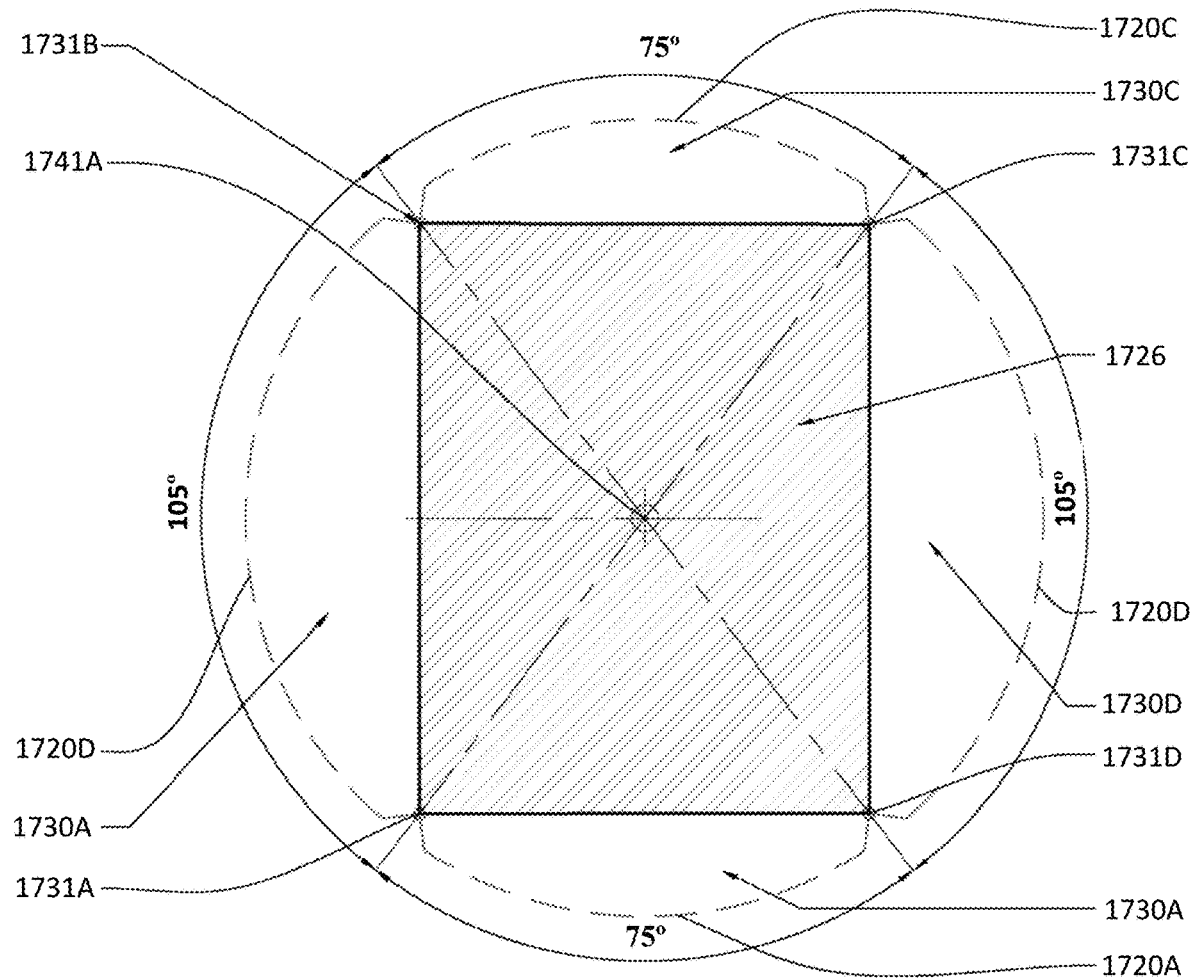

As shown in FIGS. 17A-C, there are four continuous helical flutes 1720A, 1720B, 1720C and 1720D, which are flats or grooves that follow the circumference of the working surface 1712, and spiral around the central axis 1740 toward the leading tip 1713. These flutes 1720A, 1720B, 1720C and 1720D may be equidistant from each other or become increasingly tighter or more numerous as they approach the tip 1713. Flutes 1720A, 1720B, 1720C and 1720D revolve around the central axis 1740 in either a right to left, or left to right direction. The total number of revolutions of each flute 1720A, 1720B, 1720C and 1720D between the MxFD 1717 to the MnFD 1716 are not less than one and not greater than ten. Helical flutes 1720A, 1720B, 1720C and 1720D each originate at the MxFD 1717 at separate locations. Flutes 1720A and 1720C are substantially wider than flutes 1720B and 1720D. All flutes conform to the shape of a bi-symmetric rectilinear cross-section as shown in FIGS. 17D-17G, 17K-N, 17O and 17O-1 and 17S-V. Each flute 1720A, 1720B, 1720C and 1720D is continuous along the length of the cutting surface 1712 to the leading tip 1713.

With reference to FIG. 17D-G, 17O and 17O-1, it can be seen that flutes 1720A, 1720B, 1720C, and 1720D have straight splines located between the edge tips 1731A, 1731B, 1731C, and 1731D. These splines may also be configured to be concave, convex, S-shaped or variety of other shapes useful in cutting and carrying or hauling debris away from the working surface and leading tip. As shown in FIG. 17D-G, the flutes 1720A, 1720B, 1720C, and 1720D cooperate to form a web or core 1726, which is rectilinear (i.e, rectangular in this example, but may alternatively be another four-sided shape such as a trapezoid or parallelogram). The web or core is outlined by areas of clearance designated by numerals 1730A, 1730B, 1730C, and 1730D (see FIG. 17O-1). The clearance areas 1730A, 1730B, 1730C, and 1730D can be of variable proportion and depth. Clearance areas 1730A, 1730B, 1730C, and 1730D are circumscribed by the perimeter of the cutting envelope 1743A (or 1743C).

As shown by FIGS. 17A-G, it can be seen that flutes 1720A, 1720B, 1720C, and 1720D intersect the periphery of the outer-most cutting envelope 1743A via cutting edge tips

1731A, 1731B, 1731C, and 1731D (depending on the offset). In this implementation, and as shown in FIG. 17O-1, these intersections are at 75 degrees, 105 degrees, 75 degrees, and 105 degrees of separation, forming various rake angles with the cutting envelope 1743A. In this instance, lines drawn connecting points 1731A, 1731B, 1731C, and 1731D form a bi-symmetrical rectangle. The difference in degrees between the widest flutes 1720A and 1720C and the narrowest flutes 1720B and 1720D is 30 degrees. Alternatively cutting tips cutting edge tips 1731A, 1731B, 1731C, and 1731D can intersect the cutting envelope 1734A at differing angles by increasing or decreasing the distance between the widest and narrowest flutes, for example, 100 degrees verses 80 degrees etc. Thus, the outline of the rectilinear cross-section between cutting tips 1731A, 1731B, 1731C, and 1731D can vary. The difference in the number of degrees of separation between the widest flutes and narrowest flute should not be less than 5 degrees and not greater than 70 degrees.

The depth and height of each flutes can vary, however, the cross-sectional diameter of the core portion 1726 should, in general, not be narrower than half or fifty percent of the cross sectional diameter of the instrument.

FIGS. 17H-17N are a repetition of FIGS. 17A-G, but when the instrument 1700 is fully radially constrained, e.g., confined by the ECS prior to cutting. With further reference to FIGS. 17O and 17P-V, the transition between an instrument that is a fully constrained and unconstrained can be visualized. As the instrument 1700 rotates and transitions from fully constrained to unconstrained, the center of mass path 1741 of the endodontic instrument 1700 shifts from being aligned with the axis of rotation 1740 to being a spiral around the axis of rotation 1740 (as depicted in FIGS. 17A-17G). The transition can be seen occurring in any cross-sectional view both horizontally and vertically, whereby the centroid corresponds to the axis of rotation when fully constrained and corresponds to the mass path 1741 (FIG. 17P) when unconstrained.

Referring further to FIG. 17O, the transition of the cross-sectional center of mass between a fully constrained endodontic instrument 1727C and unconstrained endodontic instrument 1727A is exemplified by distance 1744. When the instrument is unconstrained, distance 1744 generally decreases from shank to tip. During the transition the distance 1744 is variable and corresponds to the degree of constraint or relaxation of the endodontic instrument 1700 as it rotates. As the endodontic instrument 1700 is transitioning between a fully constrained endodontic instrument 1727C and unconstrained endodontic instrument 1727A, it should also be recognizable that the clearance areas 1730A-D are continuously changing such that the cutting perimeter transitions (i.e., enlarges) from cutting perimeter 1743C (when fully constrained) to cutting perimeter 1743A (when unconstrained).

In this specific implementation, the center of mass 1741 and the axis of rotation 1740 at the tip 1713 are coincident during both constrained (FIG. 17N) and unconstrained states (FIG. 17G). Other implementations are envisioned, which including a tip that maintains a constant distance away from the central axis or a variable distance.

Also in this specific implementation (as best seen in FIG. 17O), all cutting edge tips 1731A, 1731B, 1731C, and 1731D are in contact with the cutting periphery 1743C when the instrument 1700 is fully constrained. However, when the instrument 1700 is unconstrained only some cutting edge tips (e.g., cutting edge tips 1731C and 1731D in this example) are in contact with the cutting periphery 1743A. In this scenario, cutting edge tips 1731A and 1731B are not performing any cutting. Those skilled in the art will recognize numerous other implementations, for example an implementation with only one cutting edge. It should also be recognized that a myriad of rectilinear cross-sectional areas are possible, for example a trapezoid, a rhomboidal and/or a hybridization of any and all of these nuances, for example a rhomboidal cross-section with alternating cutting tips. Numerous other cross-sections are also possible, which may include a two-side or three-sided endodontic instrument. A fuller description of these cross-sections and cutting patterns follows.

Other Implementations

Although, as described above, it can be readily shown that a quadrilateral cross-section with an offset center of mass has greater torsional inertia and the potential for better resistance to cyclic fatigue than an offset triangular cross-section, other implementations are envisioned. These implementations may be particularly advantageous, if changes in metallurgy, modality of operation (reciprocation verse rotation) or other changes are employed and are as follows.

FIGS. 18A-28C illustrate three cross-sectional views of each type of endodontic instrument of multiple types of endodontic instruments (i.e., having various cross-sectional shapes such as triangular, rectangular, parallelogram, etc.). Three figures ("A," "B," and "C") are provided for each type of endodontic instrument.

Each of the FIGS. 18A-28C shows the arrangement of the instrument's cross-section in relation to the ECS wall in two ways. That is: (i) the cross-section shown in solid lines corresponds to when the instrument is not fully radially constrained, and (ii) the cross-section shown in dashed lines corresponds to when the instrument is fully radially constrained. The concentric dashed line circles bounding the gray ring shown in FIGS. 18A-28C represent two different diameters of the ECS wall. In particular, the inner dashed circle represents the ECS wall when the ECS is small in relation to the natural state of the endodontic instrument, such that the ECS fully radially constrains (compresses) the endodontic instrument. The outer dashed circle represents the ECS wall when the ECS is larger in diameter, such that the ECS does not fully radially constrain or compress the endodontic instrument.

The first cross-sectional view of each type of endodontic instrument (FIGS. 18A, 19A, 20A, 21A, 22A, 23A, 24A, 25A, 26A, 27A, and 28A) is a cross-section taken where the working body of the endodontic instrument conjoins with the shank. It can be seen that the center of mass of the cross-sections where the working body of the endodontic instrument conjoins with the shank is offset from the axis of rotation when the endodontic instrument is not fully radially constrained, and that the center of mass of the cross-sections where the working body of the endodontic instrument conjoins with the shank are coincident with the axis of rotation when the endodontic instrument is fully radially constrained. The other cross-sectional views of each type of endodontic instrument (FIGS. 18B, 18C, 19B, 19C, 20B, 20C, 21B, 21C, 22B, 22C, 23B, 23C, 24B, 24C, 25B, 25C, 26B, 26C, 27B, 27C, 28B, and 28C) are cross-sections taken along the working body of the respective endodontic instruments. In some embodiments, the tip of the endodontic instrument(s) has a center of mass that is coincident with the instrument's axis of rotation (both when the instrument is fully radially constrained and when the instrument is not fully radially constrained). In some embodiments, the tip of the endodontic instrument(s) has a center of mass that is offset from the instrument's axis of rotation when the instrument is not fully radially constrained, and that is coincident with the instrument's axis of rotation when the instrument is fully radially constrained.

Figure 18A:
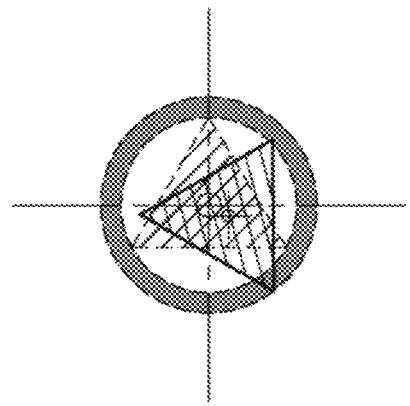
FIGS. 18A-18C depict cross-sectional views of another example endodontic instrument taken at various locations along the body of the instrument and in two conditions of diametrical constraint.
Figure 18B:
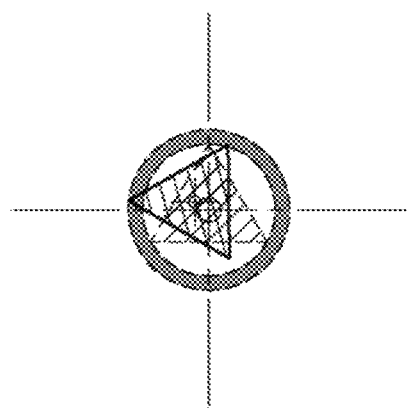
Figure 18C:
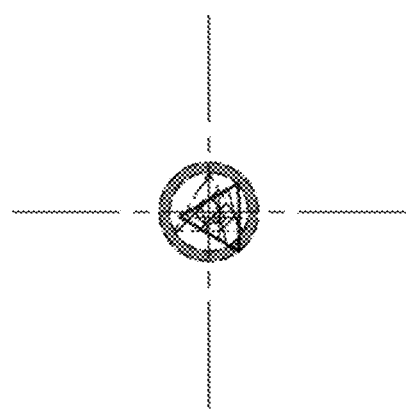

FIGS. 18A-C illustrate a flat-splined offset equilateral triangular cross-section with one or two cutting edges in contact with the ECS wall (cutting envelope), while one or two cutting edges are not in contact with the ECS wall. This implementation may prove to have lower torsional inertia than a rectilinear cross-section of similar base and height, but has the potential of being more flexible.

Figure 19A:
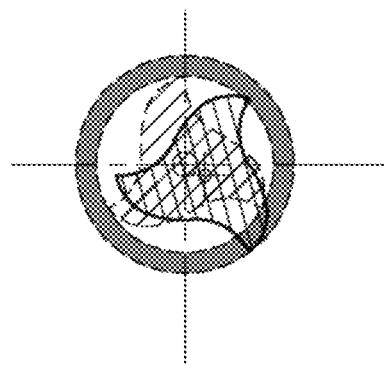
FIGS. 19A-19C depict cross-sectional views of another example endodontic instrument taken at various locations along the body of the instrument and in two conditions of diametrical constraint.
Figure 19B:
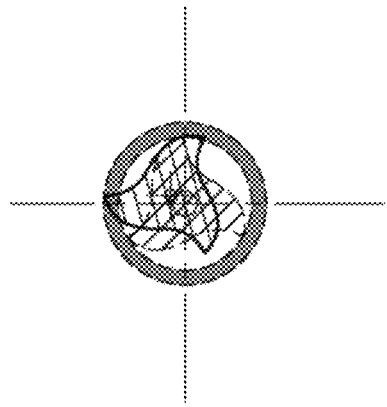
Figure 19C:
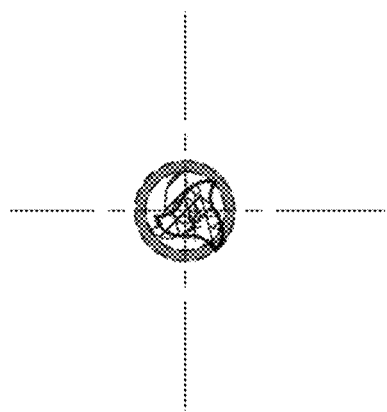

FIGS. 19A-C illustrate an offset rectilinear cross-section from shank to tip with S-shaped splines. An S-shaped spline may be more useful during cutting than a straight spline due to an improved relief angle immediately behind the lead tip. An S-shaped spline would also produce a larger clearance area and may serve to make the instrument more flexible.

Figure 20A:
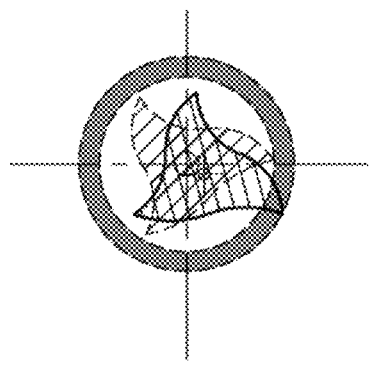
FIGS. 20A-20C depict cross-sectional views of another example endodontic instrument taken at various locations along the body of the instrument and in two conditions of diametrical constraint.
Figure 20B:
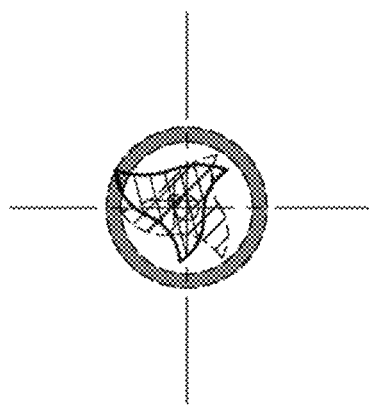
Figure 20C:
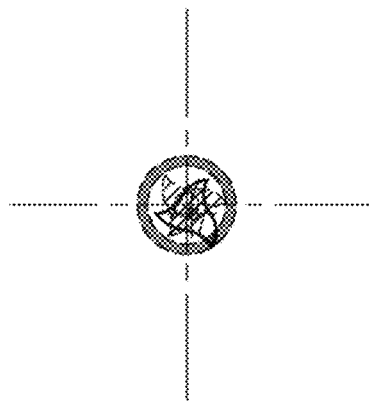

FIGS. 20A-C illustrate an offset isosceles triangular cross-section. As discussed above, asymmetrical cross-sections that are configured to revolve around the central axis of rotation can display a precessional cutting pattern. This feature in combination with an offset of the centroid have the potential of improvement in both torsional inertia and flexibility, however, these design are intrinsically less stable under power and may display some degree of "chatter" (vibration or rattling) during cutting.

Figure 21A:
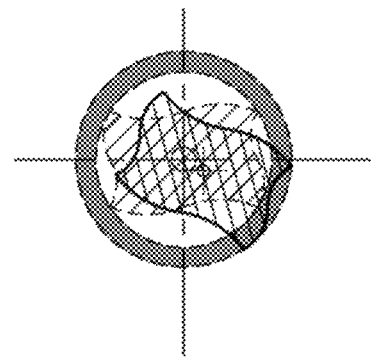
FIGS. 21A-21C depict cross-sectional views of another example endodontic instrument taken at various locations along the body of the instrument and in two conditions of diametrical constraint.
Figure 21B:
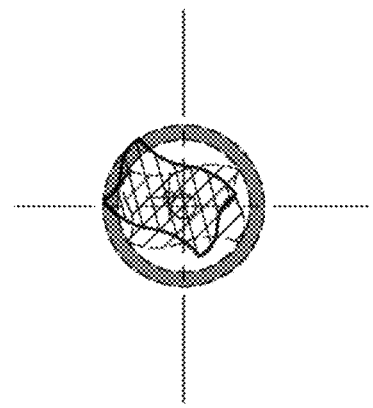
Figure 21C:
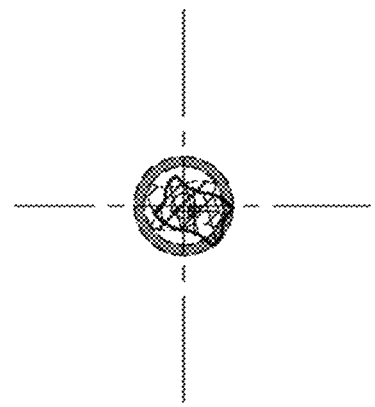

FIGS. 21A-C illustrate an S-splined offset rectangular cross-section with two cutting edges that are on the same side, but are positioned along the narrowest flutes of the cross-section. This configuration would offer improved cutting ability, but would necessarily be less resistant the torsional failure.

Figure 22A:
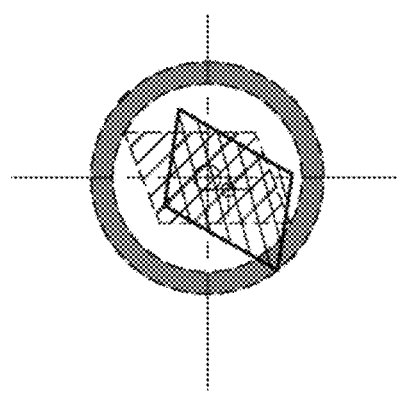
FIGS. 22A-22C depict cross-sectional views of another example endodontic instrument taken at various locations along the body of the instrument and in two conditions of diametrical constraint.
Figure 22B:
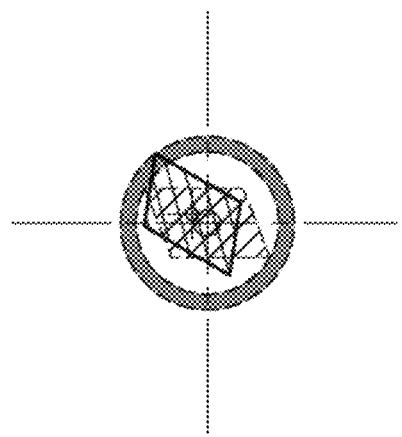
Figure 22C:
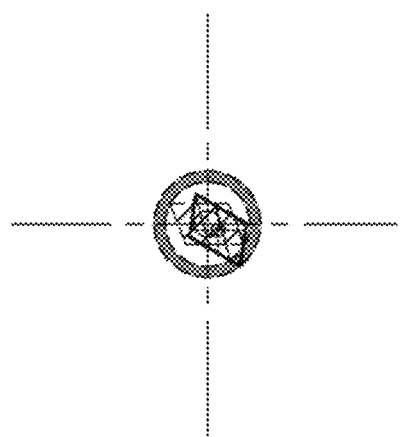

FIGS. 22A-C illustrate an offset rhomboidal cross-section with two cutting edges on opposite sides (when fully radially constrained). This implementation should be as resistant to torsional inertia as a rectangular cross-section, but may be more useful when designed for use in reciprocation or a reciprocating hand piece.

Figure 23A:
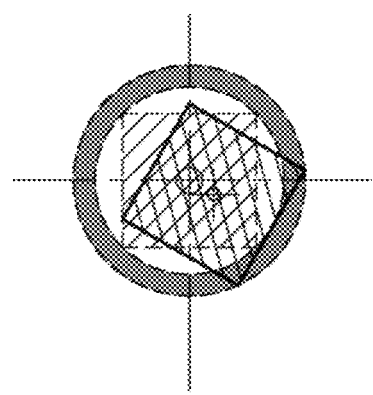
FIGS. 23A-23C depict cross-sectional views of another example endodontic instrument taken at various locations along the body of the instrument and in two conditions of diametrical constraint.
Figure 23B:
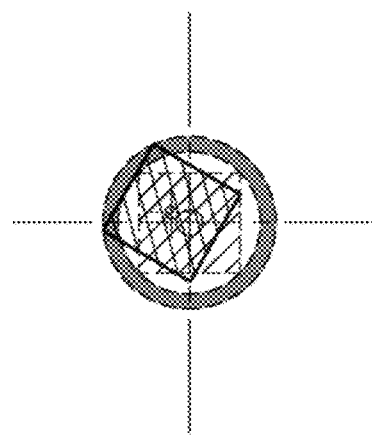
Figure 23C:
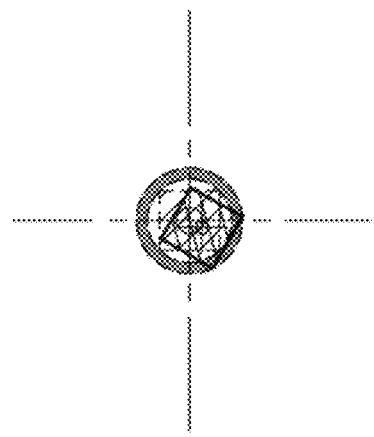

FIGS. 23A-C illustrate an offset rectilinear cross-section that is square with two cutting edges in the same side. This cross-section may be used singly or in combination with other rectilinear cross-sections that are more rectangular. For example, an instrument may retain a rectangular or rhomboidal cross-section from shank to tip, but become increasing square and end square at the tip. The tip of this would necessarily have greater torsional inertia than a rectangular tip due to the increase in the surface area itself, however, instruments with a square cross-section may be less compliant or flexible than those with rectangular cross-sections given a similar cutting envelop.

Figure 24A:
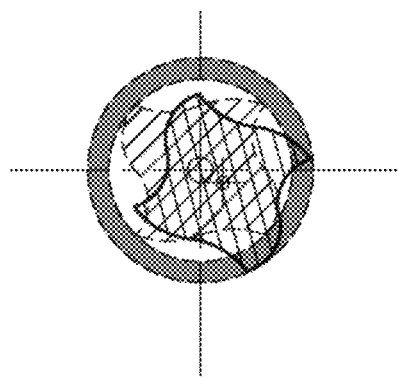
FIGS. 24A-24C depict cross-sectional views of another example endodontic instrument taken at various locations along the body of the instrument and in two conditions of diametrical constraint.
Figure 24B:
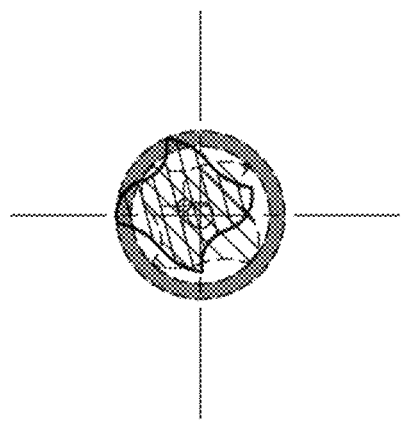
Figure 24C:
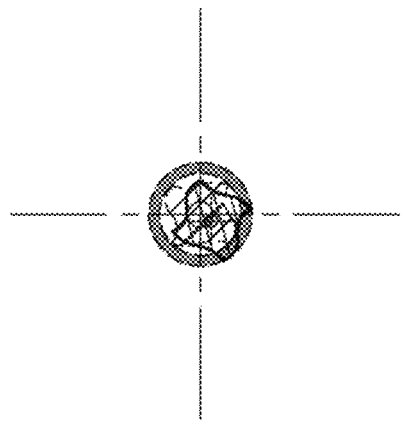

FIGS. 24A-C illustrate an offset square cross-section with S-shaped spines. An S-shaped spline may be more useful during cutting than a straight spline due to an improved relief angles and clearance angles. As previously mentioned, an instrument with a square cross-section may be have greater torsional inertia, but be less complaint or flexible than a rectangular or rhomboidal cross-sections. A hybridization of a rectangular and/or rhomboidal cross-section and a square cross-section from shank to tip is also envisioned.

Figure 25A:
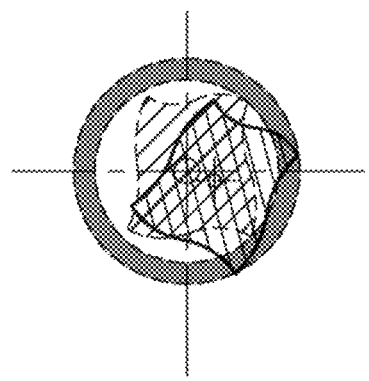
FIGS. 25A-25C depict cross-sectional views of another example endodontic instrument taken at various locations along the body of the instrument and in two conditions of diametrical constraint.
Figure 25B:
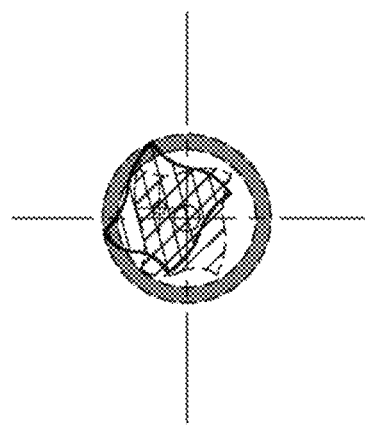
Figure 25C:
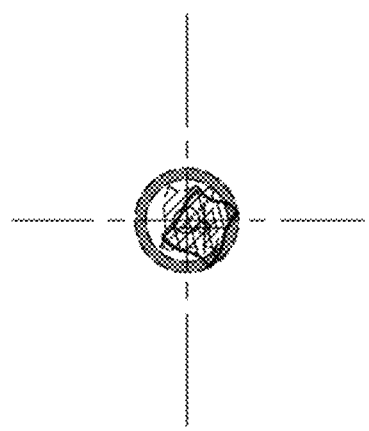

FIGS. 25A-C illustrate an offset trapezoidal cross-section with two cutting edges on the same side and along the widest cutting flute. As previously mentioned, cross-sections that are both offset and asymmetric have the potential for display excellent precessional cutting ability, but may be slightly predisposed to chatter. Instruments with four cutting edges, however, are more stable than instruments with three cutting edges and display less chatter.

Figure 26A:
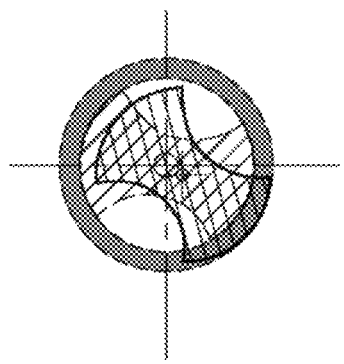
FIGS. 26A-26C depict cross-sectional views of another example endodontic instrument taken at various locations along the body of the instrument and in two conditions of diametrical constraint.
Figure 26B:
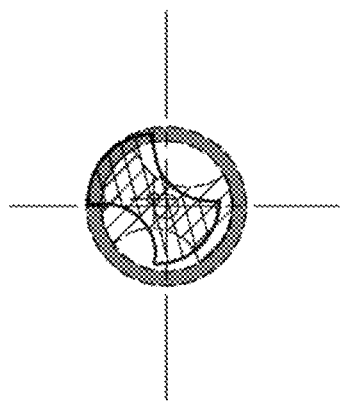
Figure 26C:
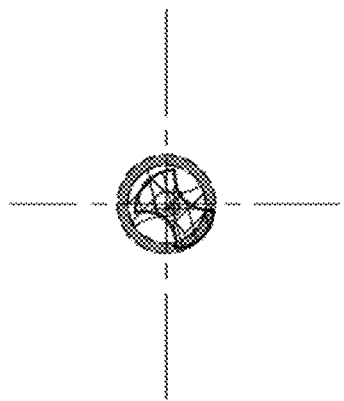

FIGS. 26A-C illustrate an offset cross-section of a "hatchet" configuration. A cross-section similar to this would be useful is an endodontic cavity preparation where a reciprocating hand piece was employed.

Figure 27A:
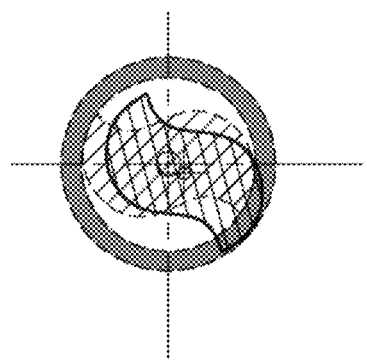
FIGS. 27A-27C depict cross-sectional views of another example endodontic instrument taken at various locations along the body of the instrument and in two conditions of diametrical constraint.
Figure 27B:
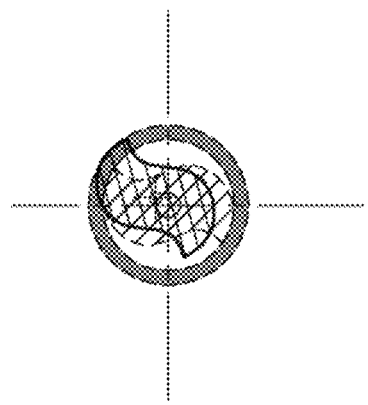
Figure 27C:
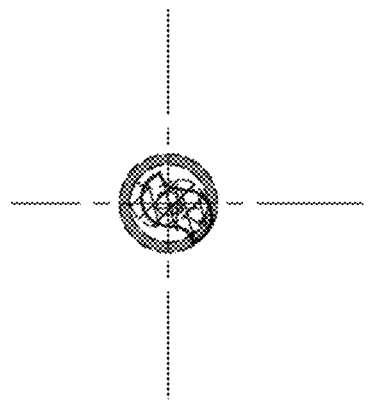

FIGS. 27A-C illustrate an offset biangular and bisymmetrical cross-section with S-shaped splines. This design may possess all the attributes of a four side cross-section with similar base and height, however, the reduced number of cutting edges may mitigate its cutting ability. This design would also be useful in reciprocation.

Figure 28A:
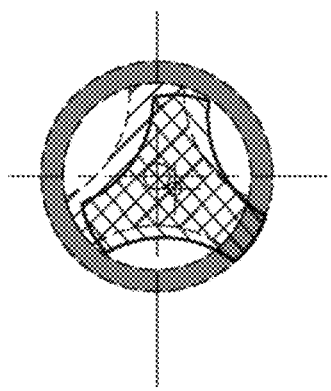
FIGS. 28A-28C depict cross-sectional views of another example endodontic instrument taken at various locations along the body of the instrument and in two conditions of diametrical constraint.
Figure 28B:
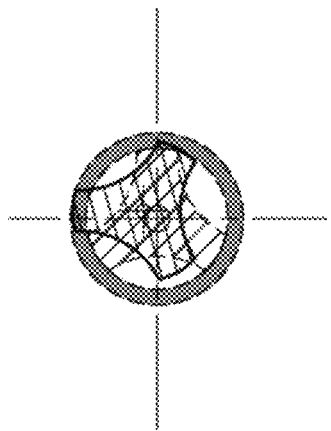
Figure 28C:
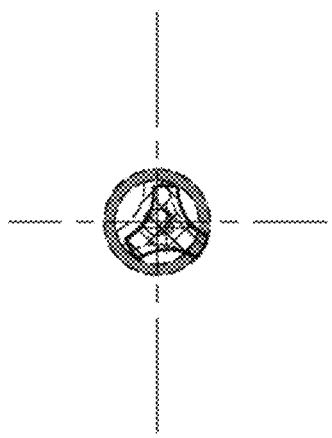

FIGS. 28A-C illustrate an offset triangular cross-section with broad radial lands. Cross-sections similar to this have also been termed U-endodontic instruments, which refers to the U-shaped clearance areas. The radial lands add bulk to the cross-section and, in turn, will add strength and appreciable resistance to torsional failure. Instruments with cross-section similar to these, however, will have efficient cutting and hauling characteristic due the increased surface tension created by the lands themselves.

Those skilled in the art could envision numerous other permutations of endodontic instrument design, when more than one of the features listed above is combined. They will also recognize that other cross-sections and features could be employed when designing a compressible endodontic instrument, which may be too numerous to mention. For example, instruments with cross-cuts, instruments with non-cutting tips and/or flutes, instruments with constant or variable tapers, instruments with variable or alternating cross-sections etc. The crux of the invention, however, is the same, and that is an endodontic instrument that is compressible with its concomitant advantages as outline above.

In summary, the unique endodontic instrument design characteristic of compressibility is described and claimed herein. Endodontic instrument compressibility is independent of the elasticity or compressibility of the material the endodontic instrument is made from. As discussed above, these characteristics are dependent on a design that has a precessional cutting axis, which is ground in or inscribed into the working portion of the instrument. A "snap shot" taken of the endodontic instrument as it rotates in a root canal shows an instrument proendodontic instrument with multiple crests and troughs (when the instrument is not fully radially compressed). The amplitude of these crests and troughs or unit distance X, translates into the degree of the off-set of the center of mass of the cross-section, which dictates not only the degree of compressibility, but the amount of stored energy available for cutting. Given a specific cross-sectional design, the instrument will be more or less flexible. Smaller cross-sectional areas will render the instrument more flexible than larger cross-sections. Instruments with more crests and troughs per unit working length will be less compressible than instruments with fewer crests and trough. And finally, instruments whereby the longitudinal axis is off-set from tip to shank or shank to tip will also display improved compressibility. In 3-dimensions, these instruments appear to revolve like a spinning top between each node. In Toto, they will appear in 3-dimensional space as a transverse helical and/or mechanical wave.

Those skilled in the art will recognized that given this large number of design variables, a larger set of instruments with differing tip diameters and tapers, both variable and constant are possible. Conversely, a single instrument with appropriate tip size, constant or variable taper and compressibility could be designed to clean and prepare a single root canal (rather than needing multiple instruments of different sizes as is the convention in the field of art currently). Finally, this design will yield an instrument with greater torsional inertia and more resistance to cyclic fatigue than instruments without an offset center of mass as dictated by the theorem for the planar moment of inertia and the parallel axis theorem.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying FIG.s do not necessarily require the particular order shown, or sequential order, to achieve desirable results. In certain implementations, multitasking and parallel processing may be advantageous.

What is claimed is:

1. A method of preparing an endodontic cavity space, the method comprising:
    inserting an endodontic instrument into the endodontic cavity space, wherein the endodontic instrument comprises:
    a shank configured for attachment to a motor to drive the endodontic instrument about a first axis, and
    a body extending from the shank by a length, the body having a working surface between: (i) a shank end portion where the working surface and the shank meet and (ii) a tip end portion where the working surface meets a tip of the endodontic instrument, the working surface including multiple edges, at least a portion of the working surface being tapered such that the tip end portion has a diameter that is less than a diameter of the shank end portion, the working surface comprising a plurality of transverse cross-sections, each transverse cross-section having a center of mass and multiple sides, the working surface having a center of mass path defined by the centers of mass of the plurality of transverse cross-sections of the body, wherein the endodontic instrument is configured to be radially compressible between: (i) an unconstrained configuration in which at least a portion of the center of mass path between the tip end portion and the shank end portion is offset from the first axis and spirals around the first axis along a length of the first axis, and (ii) a radially constrained configuration in which the portion of the center of mass path is more aligned with the first axis than in the unconstrained configuration, and preparing of the endodontic cavity space by rotating the endodontic instrument about the first axis while the endodontic instrument is in the endodontic cavity space, wherein, during the rotating, a cutting perimeter of the endodontic instrument enlarges such that the endodontic cavity space is prepared by rotating the endodontic instrument singularly, thereby eliminating a need for rotating two or more endodontic instruments of increasing sizes for the preparing of the endodontic space, and wherein, after the preparing of the endodontic cavity space by rotating the endodontic instrument singularly and without rotating two or more endodontic instruments of increasing sizes, the endodontic cavity space is sized for filling.

2. The method of claim 1, wherein during the rotating the endodontic instrument is radially compressed by the wall of the endodontic cavity space such that the center of mass path is nearer to the first axis than prior to the inserting.

3. The method of claim 1, wherein, during the rotating, one or more edges of the multiple edges are out of contact with the wall of the endodontic cavity space.

4. The method of claim 1, wherein the endodontic instrument is configured to be radially compressible to a fully radially constrained configuration in which the portion of the center of mass path is on the first axis.

5. The method of claim 1, wherein the tip of the endodontic instrument is on the first axis while the endodontic instrument is in the unconstrained configuration.

6. The method of claim 1, wherein the endodontic instrument includes four helical flutes that extend continuous along the working surface.

7. The method of claim 6, wherein each of the helical flutes has a straight spline.

8. The method of claim 6, wherein each of the helical flutes has an S-shaped spline.

9. The method of claim 1, wherein the working surface comprises a rectilinear cross-sectional shape.

10. The method of claim 9, wherein the rectilinear cross-sectional is rhomboidal.

11. The method of claim 9, wherein the rectilinear cross-sectional is trapezoidal.

12. The method of claim 9, wherein the rectilinear cross-sectional is rectangular.

13. The method of claim 9, wherein the rectilinear cross-sectional is a parallelogram.

14. The method of claim 1, wherein all edges of the multiple edges are in contact with a cutting periphery of the endodontic instrument, while the endodontic instrument is in the radially constrained configuration.

15. The method of claim 14, wherein, during the rotating, one or more edges of the multiple edges are out of contact with the wall of the endodontic cavity space.

* * * * *